US011311616B2

(12) United States Patent
Tarpey

(10) Patent No.: US 11,311,616 B2
(45) Date of Patent: Apr. 26, 2022

(54) FELINE LEUKEMIA VIRUS VACCINE

(71) Applicant: Intervet Inc., Madison, NJ (US)

(72) Inventor: Ian Tarpey, St. Ives (GB)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 16/759,927

(22) PCT Filed: Nov. 5, 2018

(86) PCT No.: PCT/EP2018/080094
§ 371 (c)(1),
(2) Date: Apr. 28, 2020

(87) PCT Pub. No.: WO2019/086646
PCT Pub. Date: May 9, 2019

(65) Prior Publication Data
US 2021/0177961 A1 Jun. 17, 2021

Related U.S. Application Data

(60) Provisional application No. 62/582,050, filed on Nov. 6, 2017, provisional application No. 62/596,508, filed on Dec. 8, 2017, provisional application No. 62/599,401, filed on Dec. 15, 2017.

(51) Int. Cl.
| | |
|---|---|
| *C12N 15/86* | (2006.01) |
| *A61K 48/00* | (2006.01) |
| *A61K 39/00* | (2006.01) |
| *C07K 14/005* | (2006.01) |
| *C07K 14/18* | (2006.01) |
| *A61K 39/21* | (2006.01) |
| *A61P 31/14* | (2006.01) |
| *C12N 7/00* | (2006.01) |

(52) U.S. Cl.
CPC .............. *A61K 39/21* (2013.01); *A61P 31/14* (2018.01); *C12N 7/00* (2013.01); *C12N 15/86* (2013.01); *A61K 2039/5256* (2013.01); *A61K 2039/5258* (2013.01); *A61K 2039/545* (2013.01); *A61K 2039/552* (2013.01); *A61K 2039/70* (2013.01); *C12N 2740/13034* (2013.01); *C12N 2740/13071* (2013.01); *C12N 2770/36143* (2013.01)

(58) Field of Classification Search
CPC ................ A61K 2300/00; C12N 15/86; C12N 2770/36143; C12N 7/00; C07K 14/005
See application file for complete search history.

(56) References Cited

U.S. PATENT DOCUMENTS

| | | | |
|---|---|---|---|
| 7,449,323 B2 | 11/2008 | Foley et al. | |
| 8,460,913 B2 | 6/2013 | Kamrud et al. | |
| 9,441,247 B2 | 9/2016 | Rayner et al. | |
| 2013/0064839 A1* | 3/2013 | Harris | C07K 14/005 424/184.1 |

FOREIGN PATENT DOCUMENTS

| | | |
|---|---|---|
| WO | 2001066568 A2 | 9/2001 |
| WO | 2017109045 A1 | 6/2017 |

OTHER PUBLICATIONS

Thomsen et al. "Expression of feline leukaemia virus gp85 and gag proteins and assembly into virus-like particles using the baculovrius expression vector system" Journal of General Virology, 1992, 73:1819-1824.*
Arjona, Alvaro et al., Seroepidemiological Survey of Infection by Feline Leukemia Virus and Immunodeficiency Virus in Madrid and Correlation with Some Clinical Aspects, Journal of Clinical Microbiology, 2000, 3448-3449, 38.
Atkins, GJ et al, Therapeutic and prophylactic applications of alphavirus vectors, Expert Reviews in Molecular Medicine, 2008, e33, 1-18, 10(1).
Braley, JO, FeLV and FIV: Survey Shows Prevalence in the United States and Europe, Feline Practice—Infectious Disease, 1994, 25-29, 22.
Bredenbeek, Peter J. et al., Sindbis Virus Expression Vectors: Packaging of RNA Replicons by Using Defective Helper RNAs, Journal of Virology, 1993, 6439-6446, 67(11).
De Noronha, F. et al., Influence of Antisera To Oncornavirus Glycoprotein (gp71) on Infections of Cats with Feline Leukemia Virus, Virology, 1978, 617-621, 85.
Flynn, J. Norman et al., Longitudinal Analysis of Feline Leukemia Virus-Specific Cytotoxic T Lymphocytes: Correlation with Recovery from Infection, Journal of Virology, 2002, 2306-2315, 76(5).
Grosenbaugh, DA et al, Comparison of the Safety and Efficacy of a Recombinant Feline Leukemia Virus (FeLV) Vaccine Delivered Transdermally and an Inactivated FeLV Vaccine Delivered Subcutaneously, Veterinary Therapeutics, Veterinary Learning Systems, 2004, 258-262, 5(4).
Hardy, Jr., William D. et al., Ten-year study comparing enzyme-linked immunosorbent assay with the immunofluorescent antibody test for detection of feline leukemia virus infection in cats, JAVMA, 1991, 1365-1373, 199(10).
Hines, David L. et al., Evaluation of efficacy and safety of an inactivated virus vaccine against feline leukemia virus infection, J. Am. Vet. Med. Assoc., 1991, 1428-1430, 199.
Hoover, Edward A. et al., Feline leukemia virus infection and diseases, J. Am. Vet. Med. Assoc., 1991, 1287-1297, 199.
Hosie, M.J. et al., Prevalence of feline leukaemia virus and antibodies to feline immunodeficiency virus in cats in the United Kingdom, Veterinary Records, 1989, 293-297, 128.
International Search Report for PCT/EP2018/080094 dated Jan. 15, 2019, 16 pages.
Kamrud, K.I. et al., Development and characterization of promoter-less helper RNAs for the production of alphavirus replicon particle, Journal of General Virology, 2010, 1723-1727, 91(Pt 7).

(Continued)

*Primary Examiner* — Barry A Chestnut
(74) *Attorney, Agent, or Firm* — Michael D. Davis

(57) ABSTRACT

The present invention provides a vaccine for feline leukemia virus and methods of making and using the vaccine alone, or in combinations with other protective agents.

20 Claims, No Drawings

Specification includes a Sequence Listing.

(56) References Cited

OTHER PUBLICATIONS

Kass, P et al, Epidemiologic evidence for a causal relation between vaccination and fibrosarcoma tumorigenesis in cats, Journal of the American Veterinary Medical Association, 1993, 396-405, 203(3).
Konopka, Jennifer L. et al., Acute Infection with Venezuelan Equine Encephalitis Virus Replicon Particles Catalyzes a Systemic Antiviral State and Protects from Lethal Virus Challenge, Journal of Virology, 2009, 12432-12442, 83(29).
Levy, Julie et al., 2008 American Association of Feline Practitioners' feline retrovirus management guidelines, Journal of Feline Medicine and Surgery, 2008, 300-316, 10.
Liljestrom, P. et al., A new generation of animal cell expression vectors based on the semliki forest virus replicon, Biotechnology, 1991, pp. 1356-1361, 9.
Liu, Chunguo et al., Complete Genome Sequence of Feline Panleukopenia Virus Strain HRB-CS1, Isolated from a Domestic Cat in Northeastern China, Genome Announcements, 2015, 1, 3(2):e01556-14.
Ljungberg, K et al, Self-replicating alphavirus RNA vaccines, Expert Review of Vaccines, 2015, 177-194, 14(2).
Lucchese, G et al, How a single amino acid change may alter the immunological information of a peptide, Frontiers in Bioscience: Elite Edition, 2012, 1843-1852, vol. 4, No. 5.
Malik, R. et al., Prevalences of feline leukaemia virus and feline immunodeficiency virus infections in cats in Sydney, Australian Veterinary Journal, 1997, 323-327, 75.
Mathes L.E. et al., Abrogation of lymphocyte blastogenesis by a feline leukaemia virus protein, Nature, 1978, 687-689, 274.
Nunberg, J.H. et al., Method to map antigenic determinants recognized by monoclonal antibodies: Localization of a determinant of virus neutralization on the feline leukemia virus envelope protein gp7O, Proc. Natl. Acad. Sci. USA, 1984, 3675-3679, 81.
Pacitti, A.M. et al., Transmission of feline leukaemia virus in the milk of a non-viraemic cat, The Veterinary Record, 1986, 381-384, 118.
Patel, M et al, Comparative Efficacy of Feline Leukemia Virus (FeLV) Inactivated Whole-Virus Vaccine and Canarypox Virus-Vectored Vaccine during Virulent FeLV Challenge and Immunosuppression, Abstract, Clinical and Vaccine Immunology, 2015, 798-805, 22(7).
Pedersen, Niels C., Immunogenicity and Efficacy of a Commercial Feline Leukemia Virus Vaccine, J. Vet. Intern. Med., 1993, 34-39, 7.
Pushko, Peter et al., Replicon-Helper Systems from Attenuated Venezuelan Equine Encephalitis Virus: Expression of Heterologous Genes in Vitro and Immunization against Heterologous Pathogens in Vivo, Virology, 1997, 389-401, 239.
Radford, Alan D. et al., Feline calicivirus. Vet. Res., 2007, 319-335, 38(2).
Rayner, JO et al., Alphavirus vectors and vaccination, Reviews in Medical Virology, 2002, pp. 279-296, 12.
Reed, DS et al, Combined Alphavirus Replicon Particle Vaccine Induces Durable and Cross-Protective Immune Responses against Equine Encephalitis Viruses, Journal of Virology, 2014, 12077-12086, vol. 88, No. 20.
Rojko, Jennifer L. et al., Pathogenesis of infection by the feline leukemia virus, J Am Vet Med Assoc, 1991, 1305-1310, 199.
Scherk, M.A., et al., 2013 AAFP Feline Vaccination Advisory Panel Report, Journal of Feline Medicine and Surgery, 2013, pp. 785-808, 15.
Scott, Fred W et al., Long-term immunity in cats vaccinated with an inactivated trivalent vaccine, Am. J. Vet. Res., 1999, 652-658, 60.
Segundo, Fayna Diaz-San et al., Venezuelan Equine Encephalitis Replicon Particles Can Induce Rapid Protection against Foot-and-Mouth Disease Virus, Journal of Virology, 2013, 5447-5460, 87(10).
Sosnovtsev, Stanislav V. et al., Identification and Genomic Mapping of the ORF3 and VPg Proteins in Feline Calicivirus Virions, Virology, 2000, 193-203, 277.
Sparkes, A.H., Feline leukaentia virus: a revie-w of immunity and vaccination, Journal of Small Animal Practice, 1997, 187-194, 38.
Stuke, K et al, Efficacy of an inactivated FeLV vaccine compared to a recombinant FeLV vaccine in minimum age cats following virulent FeLV challenge, Vaccine, 2014, 2599-2603, 32(22).
Thomsen, Darrell R. et al., Expression of feline leukaemia virus gp85 and gag proteins and assembly into virus-like particles using the baculovirus expression vector system, Journal of General Virology, 1992, 1819-1824, 73.
Torres, Andrea N. et al., Feline leukemia virus immunity induced by whole inactivated virus vaccination, Veterinary Immunology and Immunopathology, 2010, 122-131, 134.
Uematus, Y et al, Lack of Interference with Immunogenicity of a Chimeric Alphavirus Replicon Particle-Based Influenza Vaccine by Preexisting Antivector Immunity, Clinical and Vaccine Immunology, 2012, 991-998, vol. 19, No. 7.
Vander Veen, RL et al, Alphavirus replicon vaccines, Animal Health Research Reviews, 2012, 1-9, vol. 13, No. 1.

\* cited by examiner

SEQUENCE LISTING

<160> NUMBER OF SEQ ID NOS: 13

<210> SEQ ID NO 1
<211> LENGTH: 1929
<212> TYPE: DNA
<213> ORGANISM: Artificial Sequence
<220> FEATURE:
<223> OTHER INFORMATION: codon optimized for feline

<400> SEQUENCE: 1

| | | | | | |
|---|---|---|---|---|---|
| atggagtcac | caacacaccc | taaaccttct | aaagacaaaa | ccctctcgtg | gaatctcgcc | 60 |
| ttccttgtgg | gcatcctgtt | cacaatcgac | atcggcatgg | ccaacccttc | gccgcatcag | 120 |
| atctacaatg | tgacatgggt | cattactaat | gtgcagacaa | acacccaggc | aaatgctact | 180 |
| tctatgcttg | gtactctgac | tgatgcttat | ccaaccctgc | acgtcgacct | ttgcgatctc | 240 |
| gtcggtgaca | catgggagcc | catcgtgctg | aatccaacta | atgtcaaaca | tggtgccagg | 300 |
| tattcttcta | gcaaatacgg | tgtaagacc | actgatcgga | gaaacagca | acaaacctac | 360 |
| ccattctacg | tgtgcccggg | tcacgcaccg | tccctgggtc | gaagggaac | acattgtggg | 420 |
| ggagcccaag | acgttttttg | cgctgcttgg | ggttgtgaaa | caaccggaga | agcctggtgg | 480 |
| aagcctacct | catcttggga | ctacattact | gtgaaaagag | gctctagcca | ggataacagc | 540 |
| tgcgaaggaa | agtgtaatcc | cctggtgctt | caattcaccc | agaaaggccg | gcaggcatca | 600 |
| tgggatggac | cgaaaatgtg | gggacttaga | ctctatcgca | ccggatacga | ccccatcgct | 660 |
| ctgtttactg | tgtcacgcca | agtctccacc | attactccgc | cacaggccat | ggggccgaat | 720 |
| ctggtcctcc | ccgatcagaa | gccaccctca | cggcaaagtc | aaaccggctc | aaaagtggcc | 780 |
| acccaacggc | cccagacaaa | tgagtccgca | cctaggtcag | tggcacctac | aacaatgggt | 840 |
| ccaaagcgga | tcggaaccgg | agacaggctc | attaacctcg | tgcaagggac | ttatctggcc | 900 |
| cttaacgcta | ctgaccccaa | caagaccaag | gattgctggc | tctgccttgt | gagcagacct | 960 |
| ccttactatg | aggggatcgc | cattctcgga | aactactcaa | atcagaccaa | cccccctccg | 1020 |
| tcgtgtctga | gcacccccca | gcacaagctt | actatttcag | aagtcagtgg | acagggaatg | 1080 |
| tgcatcggaa | ccgtgccaaa | gactcatcaa | gccctttgca | acaaaactca | acaagggcac | 1140 |
| actggagctc | attatctcgc | cgcacctaac | gggacctact | gggcttgcaa | tactggattg | 1200 |
| accccgtgta | tctctatggc | cgtgctgaat | tggacttccg | acttctgcgt | gcttattgag | 1260 |
| ctttggccta | gagtgacata | ccatcagcct | gagtacgtct | atacccattt | cgccaaggca | 1320 |
| gtcagattcc | ggcgggagcc | tatctccctg | actgtggcct | tgatgctcgg | tggactgaca | 1380 |
| gtggaggaa | ttgcagctgg | agtcggaact | ggaaccaagg | ccctgctcga | aactgctcag | 1440 |
| ttccggcagc | tgcagatggc | catgcacact | gacatccagg | ctctggagga | atcaatttca | 1500 |
| gcccttgaga | aaagcttgac | ctcgctgtct | gaagtggtcc | tccaaaacag | gcgcggtttg | 1560 |
| gacatcctgt | tccttcaaga | gggtggtctg | tgcgccgctc | tcaaggagga | atgctgtttc | 1620 |
| tacgctgacc | ataccgggct | ggtgcgcgat | aacatggcaa | agctgcggga | acgcttgaaa | 1680 |
| cagaggcagc | aactgttcga | ctctcagcag | ggatggttcg | agggctggtt | taacaagagc | 1740 |
| ccatggttta | ccactctgat | ctcttcaatc | atgggtccac | tgctcatcct | gcttctgatt | 1800 |
| cttctcttcg | gaccgtgtat | tctcaacagg | ctggtgcagt | tgtcaaggga | cagaatctcg | 1860 |
| gtggtccagg | ccctgattct | tactcagcag | tatcagcaga | ttaagcagta | cgaccccgat | 1920 |
| cggccttga | | | | | 1929 |

```
<210> SEQ ID NO 2
<211> LENGTH: 642
<212> TYPE: PRT
<213> ORGANISM: Feline leukemia virus

<400> SEQUENCE: 2

Met Glu Ser Pro Thr His Pro Lys Pro Ser Lys Asp Lys Thr Leu Ser
1               5                   10                  15

Trp Asn Leu Ala Phe Leu Val Gly Ile Leu Phe Thr Ile Asp Ile Gly
                20                  25                  30

Met Ala Asn Pro Ser Pro His Gln Ile Tyr Asn Val Thr Trp Val Ile
            35                  40                  45

Thr Asn Val Gln Thr Asn Thr Gln Ala Asn Ala Thr Ser Met Leu Gly
        50                  55                  60

Thr Leu Thr Asp Ala Tyr Pro Thr Leu His Val Asp Leu Cys Asp Leu
65                  70                  75                  80

Val Gly Asp Thr Trp Glu Pro Ile Val Leu Asn Pro Thr Asn Val Lys
                85                  90                  95

His Gly Ala Arg Tyr Ser Ser Lys Tyr Gly Cys Lys Thr Thr Asp
            100                 105                 110

Arg Lys Lys Gln Gln Gln Thr Tyr Pro Phe Tyr Val Cys Pro Gly His
        115                 120                 125

Ala Pro Ser Leu Gly Pro Lys Gly Thr His Cys Gly Gly Ala Gln Asp
130                 135                 140

Gly Phe Cys Ala Ala Trp Gly Cys Glu Thr Thr Gly Glu Ala Trp Trp
145                 150                 155                 160

Lys Pro Thr Ser Ser Trp Asp Tyr Ile Thr Val Lys Arg Gly Ser Ser
                165                 170                 175

Gln Asp Asn Ser Cys Glu Gly Lys Cys Asn Pro Leu Val Leu Gln Phe
            180                 185                 190

Thr Gln Lys Gly Arg Gln Ala Ser Trp Asp Gly Pro Lys Met Trp Gly
        195                 200                 205

Leu Arg Leu Tyr Arg Thr Gly Tyr Asp Pro Ile Ala Leu Phe Thr Val
210                 215                 220

Ser Arg Gln Val Ser Thr Ile Thr Pro Pro Gln Ala Met Gly Pro Asn
225                 230                 235                 240

Leu Val Leu Pro Asp Gln Lys Pro Pro Ser Arg Gln Ser Gln Thr Gly
                245                 250                 255

Ser Lys Val Ala Thr Gln Arg Pro Gln Thr Asn Glu Ser Ala Pro Arg
            260                 265                 270

Ser Val Ala Pro Thr Thr Met Gly Pro Lys Arg Ile Gly Thr Gly Asp
        275                 280                 285

Arg Leu Ile Asn Leu Val Gln Gly Thr Tyr Leu Ala Leu Asn Ala Thr
290                 295                 300

Asp Pro Asn Lys Thr Lys Asp Cys Trp Leu Cys Leu Val Ser Arg Pro
305                 310                 315                 320

Pro Tyr Tyr Glu Gly Ile Ala Ile Leu Gly Asn Tyr Ser Asn Gln Thr
                325                 330                 335

Asn Pro Pro Pro Ser Cys Leu Ser Thr Pro Gln His Lys Leu Thr Ile
            340                 345                 350

Ser Glu Val Ser Gly Gln Gly Met Cys Ile Gly Thr Val Pro Lys Thr
        355                 360                 365

His Gln Ala Leu Cys Asn Lys Thr Gln Gln Gly His Thr Gly Ala His
370                 375                 380
```

```
Tyr Leu Ala Ala Pro Asn Gly Thr Tyr Trp Ala Cys Asn Thr Gly Leu
385                 390                 395                 400

Thr Pro Cys Ile Ser Met Ala Val Leu Asn Trp Thr Ser Asp Phe Cys
            405                 410                 415

Val Leu Ile Glu Leu Trp Pro Arg Val Thr Tyr His Gln Pro Glu Tyr
        420                 425                 430

Val Tyr Thr His Phe Ala Lys Ala Val Arg Phe Arg Glu Pro Ile
        435                 440                 445

Ser Leu Thr Val Ala Leu Met Leu Gly Gly Leu Thr Val Gly Gly Ile
    450                 455                 460

Ala Ala Gly Val Gly Thr Gly Thr Lys Ala Leu Leu Glu Thr Ala Gln
465                 470                 475                 480

Phe Arg Gln Leu Gln Met Ala Met His Thr Asp Ile Gln Ala Leu Glu
                485                 490                 495

Glu Ser Ile Ser Ala Leu Glu Lys Ser Leu Thr Ser Leu Ser Glu Val
                500                 505                 510

Val Leu Gln Asn Arg Arg Gly Leu Asp Ile Leu Phe Leu Gln Glu Gly
        515                 520                 525

Gly Leu Cys Ala Ala Leu Lys Glu Glu Cys Cys Phe Tyr Ala Asp His
530                 535                 540

Thr Gly Leu Val Arg Asp Asn Met Ala Lys Leu Arg Glu Arg Leu Lys
545                 550                 555                 560

Gln Arg Gln Gln Leu Phe Asp Ser Gln Gly Trp Phe Glu Gly Trp
                565                 570                 575

Phe Asn Lys Ser Pro Trp Phe Thr Thr Leu Ile Ser Ser Ile Met Gly
                580                 585                 590

Pro Leu Leu Ile Leu Leu Leu Ile Leu Leu Phe Gly Pro Cys Ile Leu
                595                 600                 605

Asn Arg Leu Val Gln Phe Val Lys Asp Arg Ile Ser Val Val Gln Ala
                610                 615                 620

Leu Ile Leu Thr Gln Gln Tyr Gln Gln Ile Lys Gln Tyr Asp Pro Asp
625                 630                 635                 640

Arg Pro

<210> SEQ ID NO 3
<211> LENGTH: 1233
<212> TYPE: DNA
<213> ORGANISM: Artificial Sequence
<220> FEATURE:
<223> OTHER INFORMATION: condon optimized for feline

<400> SEQUENCE: 3
aatcctagtc cacaccaaat atataatgta acttgggtaa taaccaatgt acaaactaac    60
acccaagcta acgccacctc tatgttagga accttaaccg atgcctaccc taccctacat   120
gttgacttat gtgacctagt gggagacacc tgggaaccta tagtcctaaa cccaaccaat   180
gtaaaacacg gggcacgtta ctcctcctca aaatatggat gtaaaactac agatagaaaa   240
aaacagcaac agacataccc cttttacgtc tgccccggac atgcccctc gttggggcca    300 aagggaacac attgtggagg ggcacaagat gggttttgtg ccgcatgggg atgtgagacc   360
accggagaag cttggtggaa gcccacctcc tcatgggact atatcacagt aaaaagaggg   420
agtagtcagg acaatagctg tgagggaaaa tgcaaccccc tggttttgca gttcacccag   480
aagggaagac aagcctcttg gacggacct aagatgtggg gattgcgact ataccgtaca    540
ggatatgacc ctatcgcttt attcacggtg tcccggcagg tatcaaccat tacgccgcct   600
```

```
caggcaatgg gaccaaacct agtcttacct gatcaaaaac ccccatcccg acaatctcaa    660
acagggtcca aagtggcgac ccagaggccc caaacgaatg aaagcgcccc aaggtctgtt    720
gcccccacca ccatgggtcc caaacggatt gggaccggag ataggttaat aaatttagta    780
caagggacat acctagcctt aaatgccacc gaccccaaca aaactaaaga ctgttggctc    840
tgcctggttt ctcgaccacc ctattacgaa gggattgcaa tcttaggtaa ctacagcaac    900
caaacaaacc cccccccatc ctgcctatct actccgcaac acaaactaac tatatctgaa    960
gtatcagggc aaggaatgtg catagggact gttcctaaaa cccaccaggc tttgtgcaat   1020
aagacacaac agggacatac aggggcgcac tatctagccg cccccaacgg cacctattgg   1080
gcctgtaaca ctggactcac cccatgcatt tccatggcgg tgctcaattg gacctctgat   1140
ttttgtgtct taatcgaatt atggcccaga gtgacttacc atcaacccga atatgtgtac   1200
acacattttg ccaaagctgt caggttccga aga                                1233
```

<210> SEQ ID NO 4
<211> LENGTH: 411
<212> TYPE: PRT
<213> ORGANISM: Feline leukemia virus

<400> SEQUENCE: 4

```
Asn Pro Ser Pro His Gln Ile Tyr Asn Val Thr Trp Val Ile Thr Asn
1               5                   10                  15

Val Gln Thr Asn Thr Gln Ala Asn Ala Thr Ser Met Leu Gly Thr Leu
            20                  25                  30

Thr Asp Ala Tyr Pro Thr Leu His Val Asp Leu Cys Asp Leu Val Gly
        35                  40                  45

Asp Thr Trp Glu Pro Ile Val Leu Asn Pro Thr Asn Val Lys His Gly
    50                  55                  60

Ala Arg Tyr Ser Ser Ser Lys Tyr Gly Cys Lys Thr Thr Asp Arg Lys
65                  70                  75                  80

Lys Gln Gln Gln Thr Tyr Pro Phe Tyr Val Cys Pro Gly His Ala Pro
                85                  90                  95

Ser Leu Gly Pro Lys Gly Thr His Cys Gly Gly Ala Gln Asp Gly Phe
            100                 105                 110

Cys Ala Ala Trp Gly Cys Glu Thr Thr Gly Glu Ala Trp Trp Lys Pro
        115                 120                 125

Thr Ser Ser Trp Asp Tyr Ile Thr Val Lys Arg Gly Ser Ser Gln Asp
    130                 135                 140

Asn Ser Cys Glu Gly Lys Cys Asn Pro Leu Val Leu Gln Phe Thr Gln
145                 150                 155                 160

Lys Gly Arg Gln Ala Ser Trp Asp Gly Pro Lys Met Trp Gly Leu Arg
                165                 170                 175

Leu Tyr Arg Thr Gly Tyr Asp Pro Ile Ala Leu Phe Thr Val Ser Arg
            180                 185                 190

Gln Val Ser Thr Ile Thr Pro Pro Gln Ala Met Gly Pro Asn Leu Val
        195                 200                 205

Leu Pro Asp Gln Lys Pro Pro Ser Arg Gln Ser Gln Thr Gly Ser Lys
    210                 215                 220

Val Ala Thr Gln Arg Pro Gln Thr Asn Glu Ser Ala Pro Arg Ser Val
225                 230                 235                 240

Ala Pro Thr Thr Met Gly Pro Lys Arg Ile Gly Thr Gly Asp Arg Leu
                245                 250                 255
```

| | | | | | | | | | | | |
|---|---|---|---|---|---|---|---|---|---|---|---|
|Ile|Asn|Leu|Val|Gln|Gly|Thr|Tyr|Leu|Ala|Leu|Asn|Ala|Thr|Asp|Pro|
| | | |260| | | |265| | | |270|

Asn Lys Thr Lys Asp Cys Trp Leu Cys Leu Val Ser Arg Pro Pro Tyr
            275                 280                 285

Tyr Glu Gly Ile Ala Ile Leu Gly Asn Tyr Ser Asn Gln Thr Asn Pro
        290                 295                 300

Pro Pro Ser Cys Leu Ser Thr Pro Gln His Lys Leu Thr Ile Ser Glu
305                 310                 315                 320

Val Ser Gly Gln Gly Met Cys Ile Gly Thr Val Pro Lys Thr His Gln
                325                 330                 335

Ala Leu Cys Asn Lys Thr Gln Gln Gly His Thr Gly Ala His Tyr Leu
            340                 345                 350

Ala Ala Pro Asn Gly Thr Tyr Trp Ala Cys Asn Thr Gly Leu Thr Pro
        355                 360                 365

Cys Ile Ser Met Ala Val Leu Asn Trp Thr Ser Asp Phe Cys Val Leu
370                 375                 380

Ile Glu Leu Trp Pro Arg Val Thr Tyr His Gln Pro Glu Tyr Val Tyr
385                 390                 395                 400

Thr His Phe Ala Lys Ala Val Arg Phe Arg Arg
                405                 410

<210> SEQ ID NO 5
<211> LENGTH: 1638
<212> TYPE: DNA
<213> ORGANISM: Artificial Sequence
<220> FEATURE:
<223> OTHER INFORMATION: codon optimized for feline

<400> SEQUENCE: 5

```
atggctgacg acggatctgt gaccacccca gaacaaggaa caatggtcgg aggagtgatt      60
gccgaaccca gcgctcagat gtcaactgcg gcggacatgg cctccggaaa gtcggtggac     120
tccgagtggg aagccttctt ctcgttccac acgtccgtga actggagcac ctccgaaacc     180
caaggaaaga tcctcttcaa gcagtccctg gtcccctgc tgaacccgta cctggagcac     240
atcagcaagt gtacgtcgc ttggagcggg tcgatcgaag tgcgattttc catctcggga     300
agcggcgtgt cggtggtaa actggccgcc atcgtcgtgc cgcctggtgt cgaccctgtc     360
cagtcaacct ccatgctgca gtacccgcac gtcctgttcg acgcaagaca gtggagcca     420
gtgatcttct ccatcccgga cctccgcaac agcctgtatc acttgatgtc cgataccgat     480
accacttccc tcgtgatcat ggtgtacaac gatctgatca cccgtacgc caatgactcc     540
aacagctcgg gttgcatcgt gaccgtcgaa cgaagcctg gcatcgattt caagtttcat     600
ctgctgaaac cgcccggatc catgcttact cacgggtcca tcccttccga tctgatcccc     660
aagagctcct ccctgtggat tgggaaccgc cactggaccg atattaccga tttcgtgatt     720
cggccttttcg tgttccaagc caaccggcac ttcgacttca accaggagac tgccggctgg     780
tcaactccac ggttccgccc attggccgtg actgtgtcgc agtcaaaggg agccaagctc     840
gggaacggca tcgccaccga ctacattgtg cctggaatcc ccgacggatg gcctgatact     900
accatcccca ccaagctgac ccctaccgga gattacgcca tcacctcctc cgacggcaat     960
gatattgaaa ccaagctgga atacgagaac gcggacgtga ttaagaacaa caccaacttc    1020
cgctccatgt atatctgcgg aagcctccag agggcttggg gcgacaagaa gatcagcaac    1080
accgggttca tcactaccgg agtgattct gacaactcca tcagcccttc gaacacaatt    1140
gaccagtcca agatcgtggt gtaccaggac aaccatgtca attcggaggt ccagactagc    1200
```

```
gacatcactc ttgccatcct gggctacacc ggaattggag aagaggccat aggcgccaac    1260
cgggactccg tcgtgagaat ttccgtgctt ccggaaactg gagcaagggg cggaaatcac    1320
cccatcttct acaaaaattc catgaagctg ggctacgtga tctcctccat tgacgtgttc    1380
aactcccaaa tcctccacac ctcgcgccag ctgtcactga caactactt gttgcccct    1440 gactccttcg cggtgtaccg gattattgac agcaacggat catggttcga cattgggatt    1500
gacagcgatg ggttttcatt cgtgggcgtg tcgtcatttc aaagctgga gtttccgctg    1560 tccgcctcat acatgggcat ccagctcgca aagatccggc tggcgtccaa catccggtca    1620
tccatgacta agctgtga                                                  1638
```

<210> SEQ ID NO 6
<211> LENGTH: 545
<212> TYPE: PRT
<213> ORGANISM: Feline calicivirus

<400> SEQUENCE: 6

```
Met Ala Asp Asp Gly Ser Val Thr Thr Pro Glu Gln Gly Thr Met Val
1               5                   10                  15

Gly Gly Val Ile Ala Glu Pro Ser Ala Gln Met Ser Thr Ala Ala Asp
            20                  25                  30

Met Ala Ser Gly Lys Ser Val Asp Ser Glu Trp Glu Ala Phe Phe Ser
        35                  40                  45

Phe His Thr Ser Val Asn Trp Ser Thr Ser Glu Thr Gln Gly Lys Ile
    50                  55                  60

Leu Phe Lys Gln Ser Leu Gly Pro Leu Leu Asn Pro Tyr Leu Glu His
65                  70                  75                  80

Ile Ser Lys Leu Tyr Val Ala Trp Ser Gly Ser Ile Glu Val Arg Phe
                85                  90                  95

Ser Ile Ser Gly Ser Gly Val Phe Gly Gly Lys Leu Ala Ala Ile Val
            100                 105                 110

Val Pro Pro Gly Val Asp Pro Val Gln Ser Thr Ser Met Leu Gln Tyr
        115                 120                 125

Pro His Val Leu Phe Asp Ala Arg Gln Val Glu Pro Val Ile Phe Ser
    130                 135                 140

Ile Pro Asp Leu Arg Asn Ser Leu Tyr His Leu Met Ser Asp Thr Asp
145                 150                 155                 160

Thr Thr Ser Leu Val Ile Met Val Tyr Asn Asp Leu Ile Asn Pro Tyr
                165                 170                 175

Ala Asn Asp Ser Asn Ser Ser Gly Cys Ile Val Thr Val Glu Thr Lys
            180                 185                 190

Pro Gly Ile Asp Phe Lys Phe His Leu Leu Lys Pro Pro Gly Ser Met
        195                 200                 205

Leu Thr His Gly Ser Ile Pro Ser Asp Leu Ile Pro Lys Ser Ser Ser
    210                 215                 220

Leu Trp Ile Gly Asn Arg His Trp Thr Asp Ile Thr Asp Phe Val Ile
225                 230                 235                 240

Arg Pro Phe Val Phe Gln Ala Asn Arg His Phe Asp Phe Asn Gln Glu
                245                 250                 255

Thr Ala Gly Trp Ser Thr Pro Arg Phe Arg Pro Leu Ala Val Thr Val
            260                 265                 270

Ser Gln Ser Lys Gly Ala Lys Leu Gly Asn Gly Ile Ala Thr Asp Tyr
        275                 280                 285
```

```
Ile Val Pro Gly Ile Pro Asp Gly Trp Pro Asp Thr Thr Ile Pro Thr
290                 295                 300
Lys Leu Thr Pro Thr Gly Asp Tyr Ala Ile Thr Ser Ser Asp Gly Asn
305                 310                 315                 320
Asp Ile Glu Thr Lys Leu Glu Tyr Glu Asn Ala Asp Val Ile Lys Asn
                325                 330                 335
Asn Thr Asn Phe Arg Ser Met Tyr Ile Cys Gly Ser Leu Gln Arg Ala
            340                 345                 350
Trp Gly Asp Lys Lys Ile Ser Asn Thr Gly Phe Ile Thr Thr Gly Val
        355                 360                 365
Ile Ser Asp Asn Ser Ile Ser Pro Ser Asn Thr Ile Asp Gln Ser Lys
370                 375                 380
Ile Val Val Tyr Gln Asp Asn His Val Asn Ser Glu Val Gln Thr Ser
385                 390                 395                 400
Asp Ile Thr Leu Ala Ile Leu Gly Tyr Thr Gly Ile Gly Glu Glu Ala
                405                 410                 415
Ile Gly Ala Asn Arg Asp Ser Val Val Arg Ile Ser Val Leu Pro Glu
            420                 425                 430
Thr Gly Ala Arg Gly Gly Asn His Pro Ile Phe Tyr Lys Asn Ser Met
        435                 440                 445
Lys Leu Gly Tyr Val Ile Ser Ser Ile Asp Val Phe Asn Ser Gln Ile
450                 455                 460
Leu His Thr Ser Arg Gln Leu Ser Leu Asn Asn Tyr Leu Leu Pro Pro
465                 470                 475                 480
Asp Ser Phe Ala Val Tyr Arg Ile Ile Asp Ser Asn Gly Ser Trp Phe
                485                 490                 495
Asp Ile Gly Ile Asp Ser Asp Gly Phe Ser Phe Val Gly Val Ser Ser
            500                 505                 510
Phe Pro Lys Leu Glu Phe Pro Leu Ser Ala Ser Tyr Met Gly Ile Gln
        515                 520                 525
Leu Ala Lys Ile Arg Leu Ala Ser Asn Ile Arg Ser Ser Met Thr Lys
530                 535                 540
Leu
545

<210> SEQ ID NO 7
<211> LENGTH: 1629
<212> TYPE: DNA
<213> ORGANISM: Artificial Sequence
<220> FEATURE:
<223> OTHER INFORMATION: codon optimized for feline

<400> SEQUENCE: 7
atgactgccc cggaacaagg aacgatggtc ggaggagtga ttgcagaacc gtcagcacag    60
atgtccaccg ctgccgacat ggccactgga agagcgtgg actccgaatg ggaagccttc   120
ttctccttcc acacttcggt caactggtcg actagcgaaa cccagggga gattttgttc    180 aagcaatccc tcggccctct gctgaacccc tacctggagc atctggccaa gctgtacgtg   240
gcatggtcgg gcagcatcga agtgcgcttt agcatttccg gctccggagt gttcggggga   300
aagcttgctg ccattgtcgt gccgccagga gtggaccccg tgcagtccac ttctatgctc   360
caatacccgc atgtcctgtt cgacgccaga caggtggagc ctgtgatctt tgcctgccg   420 gatctcaggt ccaccctgta tcacctcatg tccgacaccg acaccacctc gctcgtgatc   480
atggtgtaca cgacctgat caacccctac gctaacgacg ccaacagctc aggttgcatt   540
```

```
gtgactgtcg aaaccaagcc aggccctgac ttcaagtttc atttgctgaa gccgccggt     600 tccatgctga cccacggctc gatcccatcc gacctgatcc caagacgag ctccctgtgg    660 atcggaaacc gctactggtc cgatattacc gacttcgtga tcagaccatt cgtgttccaa    720
gccaaccgcc atttcgactt caaccaggaa accgcaggat ggtcgacccc tcgattccgc    780
ccgatttcag tgaccatcac cgaacagaac ggcgcgaagc tgggaattgg cgtggcgacc    840
gactacatcg tgccgggaat cccggatgga tggcctgata cgaccattcc cggggagctg    900
atccctgccg gggactacgc catcaccaac ggtactggaa acgacatcac cactgccacc    960
ggttacgaca ccgccgacat cataaagaac aacaccaact tcagaggaat gtacatttgc   1020
ggctccctgc aacgcgcttg gggtgacaaa aagatctcga acactgcctt catcacaaca   1080
gcgactctgg acggcgataa caacaacaag atcaatcctt gtaataccat cgaccagtcc   1140
aaaatcgtgg tgttccagga taaccacgtg ggaaagaagg cgcagacctc cgacgacact   1200
ctggcgctgc ttggctacac cgggatcggc gagcaggcca ttggaagcga tcgggatcgg   1260
gtcgtgcgga tctccaccct ccccgagact ggagcaaggg gaggcaacca ccccatcttt   1320
tacaaaaaca gcattaagct cggatacgtc atccgctcca tcgatgtgtt caactctcaa   1380
atcctgcaca cttcgcggca gctgtccctg aaccactacc tcttgccgcc cgactccttc   1440
gccgtctacc ggatcattga ttcgaacggg agctggttcg acatcggcat tgatagcgat   1500
ggcttctcgt ttgtgggcgt gtcgggcttc gggaagctgg agttcccact gagcgcctca   1560
tacatgggta tccagctggc caagatcagg ctggcctcca acatccgctc acctatgact   1620
aagctgtga                                                          1629
```

<210> SEQ ID NO 8
<211> LENGTH: 542
<212> TYPE: PRT
<213> ORGANISM: Feline calicivirus

<400> SEQUENCE: 8

```
Met Thr Ala Pro Glu Gln Gly Thr Met Val Gly Gly Val Ile Ala Glu
1               5                   10                  15

Pro Ser Ala Gln Met Ser Thr Ala Ala Asp Met Ala Thr Gly Lys Ser
            20                  25                  30

Val Asp Ser Glu Trp Glu Ala Phe Phe Ser Phe His Thr Ser Val Asn
        35                  40                  45

Trp Ser Thr Ser Glu Thr Gln Gly Lys Ile Leu Phe Lys Gln Ser Leu
    50                  55                  60

Gly Pro Leu Leu Asn Pro Tyr Leu Glu His Leu Ala Lys Leu Tyr Val
65                  70                  75                  80

Ala Trp Ser Gly Ser Ile Glu Val Arg Phe Ser Ile Ser Gly Ser Gly
                85                  90                  95

Val Phe Gly Gly Lys Leu Ala Ala Ile Val Val Pro Pro Gly Val Asp
            100                 105                 110

Pro Val Gln Ser Thr Ser Met Leu Gln Tyr Pro His Val Leu Phe Asp
        115                 120                 125

Ala Arg Gln Val Glu Pro Val Ile Phe Cys Leu Pro Asp Leu Arg Ser
    130                 135                 140

Thr Leu Tyr His Leu Met Ser Asp Thr Asp Thr Thr Ser Leu Val Ile
145                 150                 155                 160

Met Val Tyr Asn Asp Leu Ile Asn Pro Tyr Ala Asn Asp Ala Asn Ser
                165                 170                 175
```

Ser Gly Cys Ile Val Thr Val Glu Thr Lys Pro Gly Pro Asp Phe Lys
            180                 185                 190

Phe His Leu Leu Lys Pro Pro Gly Ser Met Leu Thr His Gly Ser Ile
            195                 200                 205

Pro Ser Asp Leu Ile Pro Lys Thr Ser Ser Leu Trp Ile Gly Asn Arg
210                 215                 220

Tyr Trp Ser Asp Ile Thr Asp Phe Val Ile Arg Pro Phe Val Phe Gln
225                 230                 235                 240

Ala Asn Arg His Phe Asp Phe Asn Gln Glu Thr Ala Gly Trp Ser Thr
            245                 250                 255

Pro Arg Phe Arg Pro Ile Ser Val Thr Ile Thr Glu Gln Asn Gly Ala
            260                 265                 270

Lys Leu Gly Ile Gly Val Ala Thr Asp Tyr Ile Val Pro Gly Ile Pro
            275                 280                 285

Asp Gly Trp Pro Asp Thr Thr Ile Pro Gly Glu Leu Ile Pro Ala Gly
            290                 295                 300

Asp Tyr Ala Ile Thr Asn Gly Thr Gly Asn Asp Ile Thr Thr Ala Thr
305                 310                 315                 320

Gly Tyr Asp Thr Ala Asp Ile Ile Lys Asn Asn Thr Asn Phe Arg Gly
            325                 330                 335

Met Tyr Ile Cys Gly Ser Leu Gln Arg Ala Trp Gly Asp Lys Lys Ile
            340                 345                 350

Ser Asn Thr Ala Phe Ile Thr Thr Ala Thr Leu Asp Gly Asp Asn Asn
            355                 360                 365

Asn Lys Ile Asn Pro Cys Asn Thr Ile Asp Gln Ser Lys Ile Val Val
            370                 375                 380

Phe Gln Asp Asn His Val Gly Lys Lys Ala Gln Thr Ser Asp Asp Thr
385                 390                 395                 400

Leu Ala Leu Leu Gly Tyr Thr Gly Ile Gly Glu Gln Ala Ile Gly Ser
            405                 410                 415

Asp Arg Asp Arg Val Val Arg Ile Ser Thr Leu Pro Glu Thr Gly Ala
            420                 425                 430

Arg Gly Gly Asn His Pro Ile Phe Tyr Lys Asn Ser Ile Lys Leu Gly
            435                 440                 445

Tyr Val Ile Arg Ser Ile Asp Val Phe Asn Ser Gln Ile Leu His Thr
450                 455                 460

Ser Arg Gln Leu Ser Leu Asn His Tyr Leu Leu Pro Pro Asp Ser Phe
465                 470                 475                 480

Ala Val Tyr Arg Ile Ile Asp Ser Asn Gly Ser Trp Phe Asp Ile Gly
            485                 490                 495

Ile Asp Ser Asp Gly Phe Ser Phe Val Gly Val Ser Gly Phe Gly Lys
            500                 505                 510

Leu Glu Phe Pro Leu Ser Ala Ser Tyr Met Gly Ile Gln Leu Ala Lys
            515                 520                 525

Ile Arg Leu Ala Ser Asn Ile Arg Ser Pro Met Thr Lys Leu
            530                 535                 540

<210> SEQ ID NO 9
<211> LENGTH: 13
<212> TYPE: DNA
<213> ORGANISM: Artificial Sequence
<220> FEATURE:
<223> OTHER INFORMATION: 5' flanking sequence

<400> SEQUENCE: 9

```
ggcgcgccgc acc                                                        13
```

<210> SEQ ID NO 10
<211> LENGTH: 1929
<212> TYPE: RNA
<213> ORGANISM: Artificial Sequence
<220> FEATURE:
<223> OTHER INFORMATION: codon optimized for feline

<400> SEQUENCE: 10

```
auggagucac caacacaccc uaaaccuucu aaagacaaaa cccucucgug gaaucucgcc     60
uuccuugugg gcauccuguu cacaaucgac aucggcaugg ccaacccuuc gccgcaucag    120
aucuacaaug ugacaugggu cauuacuaau gugcagacaa cacccaggc aaaugcuacu     180
ucuaugcuug guacucugac ugaugcuuau ccaacccugc acgucgaccu uugcgaucuc    240
gucggugaca cauggggagcc caucgugcug aauccaacua augucaaaca ugguugccagg  300
uauucuucua gcaaauacgg guguaagacc cugaucggga agaaacagca acaaaccuac    360
ccauucuacg ugugcccggg ucacgcaccg ucccuggguc cgaagggaac acauugugggg  420
ggagcccaag acgguuuuug cgcugcuugg gguugugaaa aaccggaga agccuggugg    480
aagccuaccu caucuuggga cuacauuacu gugaaaagag gcucuagcca ggauaacagc    540
ugcgaaggaa aguguaaucc ccuggugcuu caauucaccc agaaaggccg gcaggcauca    600
ugggauggac cgaaaaugug gggacuuaga cucuaucgca ccggauacga ccccaucgcu    660
cuguuuacug ugucacgcca agucuccacc auuacuccgc cacaggccau ggggccgaau    720
cugguccucc ccgaucagaa gccacccuca cggcaaaguc aaaccggcuc aaaaguggcc    780
acccaacggc cccagacaaa ugaguccgca ccuaggucag uggcaccuac aacaaugggu    840
ccaaagcgga ucgaaccggg agacaggcuc auuaaccucg gcaagggac uuaucuggcc    900
cuuaacgcua cugaccccaa caagaccaag gauugcuggc ucugccuugu gagcagaccu    960
ccuuacuaug agggggaucgc cauucucgga aacuacucaa aucagaccaa ccccccuccg   1020
ucgugucuga gcaccccccca gcacaagcuu acuauuucag aagucagugg acaggggaaug  1080
ugcaucggaa ccgugccaaa gacucaucaa gcccuuugca caaaaacuca caagggcac    1140
acuggagcuc auuaucucgc cgcaccuaac gggaccuacu gggcuugcaa uacuggauug   1200
accccgugua ucucuauggc cgugcugaau uggacuccg acuucugcgu gcuuauugag   1260
cuuuggccua gagugacaua ccaucagccu gaguacgucu auacccauu cgccaaggca  1320
gucagauucc ggcgggagcc uaucucccug acuguggccu ugaugcucgg uggacugaca  1380
gugggaggaa uugcagcugg agucggaacu ggaaccaagg cccugcucga aacugcucag  1440
uuccggcagc ugcagauggc caugcacacu gacauccagg cucuggagga aucaauuuca  1500
gcccuugaga aaagcuugac cucgcugucu gaaguggucc ucaaaacag gcgcgguuug   1560
gacauccugu uccuucaaga ggguggcucu ugcgccgcuc ucaaggagga augcuguuuc  1620
uacgcugacc auaccgggcu ggugcgcgau aacauggcaa agcugcggga acgcuugaaa  1680
cagaggcagc aacuguucga cucucagcag ggauggucg agggcugguu uaacaagagc    1740
ccauggguua ccacucugau cucuucaauc auggguccac ugcucauccu gcuucgauu   1800
cuucucuucg gaccguguau ucaacagg cuggugcagu uguaaagga cagaaucucg    1860
gugguccagg cccugauucu uacucagcag uaucagcaga uuaagcagua cgaccccgau   1920
cggccuuga                                                          1929
```

<210> SEQ ID NO 11
<211> LENGTH: 1233
<212> TYPE: RNA
<213> ORGANISM: Artificial Sequence
<220> FEATURE:
<223> OTHER INFORMATION: codon optimized for feline

<400> SEQUENCE: 11

| | | | | | |
|---|---|---|---|---|---|
| aauccuaguc | cacaccaaau | auauaaugua | acuuggguaa | uaaccaaugu | acaaacuaac | 60 |
| acccaagcua | acgccaccuc | uauguuagga | accuuaaccg | augccuaccc | uacccuacau | 120 |
| guugacuuau | ugaccuagu | gggagacacc | ugggaaccua | uagccuaaa | cccaaccaau | 180 |
| guaaaacacg | gggcacguua | cuccuccuca | aauauggau | guaaaacuac | agauagaaaa | 240 |
| aaacagcaac | agacauaccc | cuuuuacguc | ugccccggac | augccccucu | guggggcca | 300 |
| aagggaacac | auuguggagg | ggcacaagau | ggguuuugug | ccgcaugggg | augugagacc | 360 |
| accggagaag | cuugguggaa | gcccaccucc | ucaugggacu | auaucacagu | aaaaagaggg | 420 |
| aguagucagg | acaauagcug | ugagggaaaa | ugcaaccccc | ugguuuugca | guucacccag | 480 |
| aagggaagac | aagccucuug | ggacggaccu | aagauguggg | gauugcgacu | auaccguaca | 540 |
| ggauaugacc | cuaucgcuuu | auucacggug | ucccggcagg | uaucaaccau | uacgccgccu | 600 |
| caggcaaugg | gaccaaaccu | agucuuaccu | gaucaaaaac | ccccaucccg | acaaucucaa | 660 |
| acaggguccaa | aguggcgac | ccagaggccc | caaacgaaug | aaagcgcccc | aaggucuguu | 720 |
| gccccacca | ccaugggucc | caaacggauu | gggaccggag | auagguuaau | aaauuuagua | 780 |
| caagggacau | accuagccuu | aaaugccacc | gaccccaaca | aaacuaaaga | cuguuggcuc | 840 |
| ugccugguuu | cucgaccacc | cuauuacgaa | gggauugcaa | ucuuagguaa | cuacagcaac | 900 |
| caaacaaacc | ccccccauc | cugccuaucu | acuccgcaac | acaaacuaac | uauaucugaa | 960 |
| guaucagggc | aaggaaugug | cauagggacu | guuccuaaaa | cccaccaggc | uuugugcaau | 1020 |
| aagacacaac | agggacauac | aggggcgcac | uaucuagccg | cccccaacgg | caccuauugg | 1080 |
| gccuguaaca | cuggacucac | cccaugcauu | uccauggcgg | ugcucaauug | gaccucugau | 1140 |
| uuuuguucu | uaaucgaauu | auggcccaga | gugacuuacc | aucaacccga | auaugugua | 1200 |
| acacauuuug | ccaaagcugu | cagguuccga | aga | | | 1233 |

<210> SEQ ID NO 12
<211> LENGTH: 1638
<212> TYPE: RNA
<213> ORGANISM: Artificial Sequence
<220> FEATURE:
<223> OTHER INFORMATION: codon optimized for feline

<400> SEQUENCE: 12

| | | | | | |
|---|---|---|---|---|---|
| auggcugacg | acggaucugu | gaccacccca | gaacaaggaa | caauggucgg | aggagugauu | 60 |
| gccgaaccca | gcgcucagau | gucaacugcg | gcggacaugg | ccuccggaaa | gucgguggac | 120 |
| uccgagugg | aagccuucuu | cucguuccac | acgucccguga | acuggagcac | ucccgaaacc | 180 |
| caaggaaaga | uccucuucaa | gcagucccug | gguccccugc | ugaacccgua | ccuggagcac | 240 |
| aucagcaagc | uguacgucgc | cuuggagcggg | ucgaucgaag | ugcgauuuuc | caucucggga | 300 |
| agcggcgugu | cgguggugaa | acuggccgcc | aucgucguc | cgccuggugu | cgacccuguc | 360 |
| cagucaaccu | ccaugcugca | guacccgcac | guccuguucg | acgcaagaca | aguggagcca | 420 |
| gugaucuucu | ccauccccgga | ccuccgcaac | agccuguauc | acuugaugug | cgauaccgau | 480 |
| accacuuccc | ucguigaaucau | ggugacaaac | gaucugauca | acccgacgc | caaugacucc | 540 |

| | |
|---|---|
| aacagcucgg guugcaucgu gaccgucgaa acgaagccug gcaucgauuu caaguuucau | 600 |
| cugcugaaac cgcccggauc caugcuuacu cacggguccca ucccuuccga ucugaucccc | 660 |
| aagagcuccu cccuguggau ugggaaccgc cacuggaccg auauuaccga uuucgugauu | 720 |
| cggccuuucg uguccaagc caaccggcac uucgacuuca accaggagac ugccggcugg | 780 |
| ucaacuccac gguccgccc auuggccgug acugugucgc agucaaaggg agccaagcuc | 840 |
| gggaacggca ucgccaccga cuacauugug ccuggaaucc cgacggaug gccugauacu | 900 |
| accauccca ccaagcugac cccuaccgga gauuacgcca ucaccuccuc cgacggcaau | 960 |
| gauauugaaa ccaagcugga auacgagaac cggacgugga uuaagaacaa caccaacuuc | 1020 |
| cgcuccaugu auaucugcgg aagccuccag agggcuuggg gcgacaagaa gaucagcaac | 1080 |
| accggguuca ucacuaccgg agugauuucu gacaacucca ucagcccuuc gaacacaauu | 1140 |
| gaccagucca agaucguggu guaccaggac aaccaugucca auucggaggu ccagacuagc | 1200 |
| gacaucacuc uugccauccu gggcuacacc ggaauuggag aagaggccau aggcgccaac | 1260 |
| cgggacuccg ucgugagaau uccgugcuu ccggaaacug gagcaagggg cggaaaucac | 1320 |
| cccaucuucu acaaaaauuc caugaagcug ggcuacguga ucuccuccau ugacguguuc | 1380 |
| aacucccaaa uccuccacac cucgcgccag cugucacuga acaacuacuu guugcccccu | 1440 |
| gacuccuucg cgguguaccg gauuauugac agcaacggau caugguucga cauugggauu | 1500 |
| gacagcgaug gguuucauu cguggcgug ucgucauuc caaagcugga guuccgcug | 1560 |
| uccgccucau acaugggcau ccagcucgca aagauccggc uggcguccaa cauccgguca | 1620 |
| uccaugacua agcuguga | 1638 |

<210> SEQ ID NO 13
<211> LENGTH: 1629
<212> TYPE: RNA
<213> ORGANISM: Artificial Sequence
<220> FEATURE:
<223> OTHER INFORMATION: codon optimized for feline

<400> SEQUENCE: 13

| | |
|---|---|
| augacugccc cggaacaagg aacgaugguc ggaggaguga uugcagaacc gucagcacag | 60 |
| augucccaccg cugccgacau ggccacugga aagagcgugg acuccgaaug ggaagccuuc | 120 |
| uucccccuucc acacuucggu caacuggucg acuagcgaaa cccaggggaa gauuuuguuc | 180 |
| aagcaauccc ucggcccucu gcugaacccc uaccuggagc aucuggccaa gcuguacgug | 240 |
| gcauggucgg gcagcaucga agugcgcuuu agcauuuccg gcuccggagu guucgggggga | 300 |
| aagcuugcug ccauugucgu gccgccagga guggacccgg ugcagucccac uucuaugcuc | 360 |
| caauacccgc auguccuguu cgacgccaga cagguggagc cuguaucuu uugccugccg | 420 |
| gaucucaggu ccacccugua ucaccucaug uccgacaccg acaccaccuc gcucgugauc | 480 |
| augguguaca acgaccugau caaccccuac gcuaacgacg ccaacagcuc agguugcauu | 540 |
| gugacugucg aaaccaagcc aggcccgac uucaaguuuc auuugcugaa gccgccggu | 600 |
| uccaugcuga cccacggcuc gauccccauc gaccugaucc caagacgag cuccugugg | 660 |
| aucggaaacc gcuacuggucc cgauauuacc gacuucguga ucagaccauu cgucuccaa | 720 |
| gccaaccgcc auucgacuu caaccaggaa accgcaggau ggucgacccc ucgauuccgc | 780 |
| ccgauuucag ugaccaucac cgaacagaac ggcgcgaagc uggaauugg cguggcgacc | 840 |
| gacuacaucg ugccgggaau cccggaugga uggccugaua cgaccauucc cggggagcug | 900 |
| auccccugccg gggacuacgc caucaccaac gguacuggaa acgacaucac cacugccacc | 960 |

```
gguuacgaca ccgccgacau cauaaagaac aacaccaacu ucagaggaau guacauuugc    1020
ggcucccugc aacgcgcuug gggugacaaa aagaucucga acacugccuu caucacaaca    1080
gcgacucugg acggcgauaa caacaacaag aucaauccuu guaauaccau cgaccagucc    1140
aaaaucgugg uguuccagga uaaccacgug ggaaagaagg cgcagaccuc cgacgacacu    1200
cuggcgcugc uuggcuacac cgggaucggc gagcaggcca uuggaagcga ucgggaucgg    1260
gucgugcgga ucuccacccu ccccgagacu ggagcaaggg gaggcaacca ccccaucuuu    1320
uacaaaaaca gcauuaagcu cggauacguc auccgcucca ucgauguguu caacucucaa    1380
auccugcaca cuucgcggca gcugucccug aaccacuacc ucuugccgcc cgacuccuuc    1440
gccgucuacc ggaucauuga uucgaacggg agcugguucg acaucggcau ugauagcgau    1500
ggcuucucgu uugugggcgu gucgggcuuc gggaagcugg aguucccacu gagcgccuca    1560
uacaugggua uccagcuggc caagaucagg cuggccucca acauccgcuc accuaugacu    1620
aagcuguga                                                            1629
```

FELINE LEUKEMIA VIRUS VACCINE

CROSS-REFERENCE TO RELATED APPLICATIONS

This application is a national stage entry under 35 U.S.C. § 371 of PCT/EP2018/080094, filed on Nov. 5, 2018, which claims priority under 35 U.S.C. § 119(e) of provisional applications U.S. Ser. No. 62/582,050 filed Nov. 6, 2017, U.S. Ser. No. 62/596,508 filed Dec. 8, 2017, and U.S. Ser. No. 62/599,401 filed Dec. 15, 2017, the content of all of which are hereby incorporated by reference in their entireties.

FIELD OF THE INVENTION

The present invention relates to new vaccines for feline leukemia virus. Methods of making and using the vaccine alone or in combinations with other protective agents are also provided.

BACKGROUND

Feline leukemia virus (FeLV) is a retrovirus that infects domestic cats, resulting in significant morbidity and mortality worldwide. Though predominantly transmitted through saliva, FeLV also has been reported to spread through contact with body fluids [Pacitti et al., *Vet Rec* 118:381-384 (1986) doi:10.1136/vr.118.14.381; Levy et al., *J Feline Med Surg* 10:300-316 (2008) doi:10.1016/j.jfms.2008.03.002]. The clinical signs in cats observed during FeLV infections include: cytoproliferative disorders (lymphoid or myeloid tumors), cytosuppressive disorders (infectious diseases associated with immunosuppression, anemia, myelosuppression), inflammatory disorders, neurological disorders, abortions, and enteritis [Hoover et al., *J Am Vet Med Assoc* 199:1287-1297 (1991); Levy and Crawford, *Textbook of Veterinary Internal Medicine*, 6th ed (Ettinger S J, Feldman E C., eds.) WB Saunders, Philadelphia, Pa. (2005)]. The prevalence of antigenemia may vary from 1-5% in healthy cats to 15-30% in afflicted cats [Hosie et al. *Veterinary Records*, 128: 293-297 (1989); Braley, Feline Practice 22: 25-29 (1994); Malik et al., *Australian Veterinary Journal* 75:323-327 (1997); Arjona et al., *Journal of Clinical Microbiology* 38:3448-3449 (2000)]. FeLV frequently establishes a lasting infection with a concomitant persistent viremia, often leading to the death of the host cat.

The RNA genome of FeLV encodes only three genes: (i) an ENV gene, which encodes the envelope glycoprotein, (ii) a GAG gene, which encodes the major structural components of the virus, and (iii) a POL gene, which encodes the RNA polymerase [Thomsen et al., *Journal of General Virology* 73:1819-1824 (1992)]. The FeLV envelope (ENV) gene encodes a gp85 precursor protein which is proteolytically processed by one or more cellular enzymes to yield the major envelope glycoprotein gp70 and the associated transmembrane protein p15E [DeNoronha, et al., *Virology* 85:617-621 (1978); Nunberg et al., *PNAS* 81:3675-3679 (1983)]. The transmembrane protein p15E contains a sequence conserved among gammaretroviruses with immunosuppressive properties [Mathes et al., *Nature* 274:687-689 (1978)]. Recently, The European Medicines Agency's Committee for Medicinal Products for Veterinary Use (CVMP) has adopted a positive opinion for a vaccine comprising a recombinant p45 FeLV-envelope antigen derived from the gp70 surface glycoprotein of the FeLV subgroup A that is expressed in *Escherichia coli* as active substance. The FeLV envelope glycoprotein is the target of FeLV-specific cytotoxic T cell responses, as well as neutralizing antibodies and accordingly, one of the major immunogens of FeLV [Flynn et al., *J. Virol.* 76(5): 2306-2315 (2002)].

A variety of factors, such as the immune status of the host, the age of the host, the infecting FeLV strain, the viral load, as well as the route of the exposure of the FeLV can all affect the ultimate outcome of that exposure. At one time veterinarians and researchers classified FeLV infections in relation to the relative persistence of the concomitant antigenemia, which in the more fortunate cases were a transient antigenemia and/or the elimination of infection. Assays for antigenemia include p27 enzyme-linked immunosorbent assay (ELISA), virus isolation, and immunofluorescence assays [Hoover et al., *J Am Vet Med Assoc* 199:1287-1297 (1991); Rojko and Kociba, *J Am Vet Med Assoc* 199:1305-1310 (1991)]. Such tests remain helpful in clinical applications, as well as for determining whether the clinical disease is a result of an actively circulating virus.

Four vaccines for FeLV are currently available in the United States, including two whole-virus adjuvanted killed vaccines; a dual-adjuvanted, multiple-antigen vaccine; and a nonadjuvanted, canarypox virus-vectored vaccine. Notably, different vaccines have been shown to have various degrees of efficacy [Sparkes, *J Small Anim Pract* 38:187-194 (1997) doi:10.1111/j.1748-5827.1997.tb03339.x.]. Earlier studies demonstrated the efficacy of whole-virus adjuvanted killed vaccines after challenge, including testing vaccinated and unvaccinated cats for viral RNA, proviral DNA, FeLV antibodies, and the p27 antigen [Hines et al., *J Am Vet Med Assoc* 199:1428-1430 (1991); Pedersen, *J Vet Intern Med* 7:34-39 (1993) doi:10.1111/j.1939-1676.1993.tb03166.x.]; Torres et al., *Vet Immunol Immunopathol* 134:122-131 (2010) doi:10.1016/j.vetimm.2009.10.017]. There are limited data evaluating the efficacy of the nonadjuvanted recombinant FeLV vaccine available for use [Stuke et al., *Vaccine* 32:2599-2603 (2014) doi:10.1016/j.vaccine.2014.03.016].

More recently, the efficacy of two commercially available feline leukemia vaccines, one an inactivated whole-virus vaccine and the other a live canarypox virus-vectored vaccine have been compared following a challenge with virulent feline leukemia virus [Patel et al., *Clinical and Vaccine Immunology* 22(7):798-805 (2015)]. In this study the whole-virus adjuvanted killed vaccine was again found to provide superior protection against FeLV infection. However, the use of whole-virus killed adjuvanted FeLV vaccines has been implicated as one factor that leads to the development of feline injection-site sarcomas [Kass et al., *J. AM Vet Med Assoc* 203 (3): 396-405 (1993)]. Although subsequent studies have been unable to establish a direct link between killed adjuvanted vaccines and feline injection-site sarcomas, a perception remains that nonadjuvanted vaccines are safer. Indeed, the American Association of Feline Practitioners Feline Vaccination Guidelines suggest the use of nonadjuvanted FeLV vaccines to lower the risk of feline injection-site sarcomas and to reduce local inflammation [*AAFP Feline Advisory Panel*, 15: 785-808 (2013)].

A number of vector strategies have been employed through the years for vaccines in an effort to protect against certain pathogens. One such vector strategy includes the use of alphavirus-derived replicon RNA particles (RP) [Vander Veen, et al. *Anim Health Res Rev.* 13(1):1-9. (2012) doi: 10.1017/S1466252312000011; Kamrud et al., *J Gen Virol.* 91(Pt 7):1723-1727 (2010)] which have been developed from several different alphaviruses, including Venezuelan equine encephalitis virus (VEE) [Pushko et al., *Virology*

239:389-401 (1997)], Sindbis (SIN) [Bredenbeek et al., *Journal of Virology* 67:6439-6446 (1993)], and Semliki Forest virus (SFV) [Liljestrom and Garoff, Biotechnology (NY) 9:1356-1361 (1991)]. RP vaccines deliver propagation-defective alphavirus RNA replicons into host cells and result in the expression of the desired antigenic transgene(s) in vivo [Pushko et al., *Virology* 239(2):389-401 (1997)]. RPs have an attractive safety and efficacy profile when compared to some traditional vaccine formulations [Vander Veen, et al. *Anim Health Res Rev.* 13(1):1-9. (2012)]. The RP platform has been used to encode pathogenic antigens and is the basis for several USDA-licensed vaccines for swine and poultry.

Unfortunately heretofore, pet owners were forced to choose between (i) nonadjuvanted FeLV vaccines that were believed to be safer, but found to be significantly less efficacious than killed, adjuvanted vaccines [see, Stuke et al., Vaccine 32: 2599-2603 (2014); Patel et al., *Clin Vaccine Immunol* 22 (7):798-808 (2015)] and (ii) the adjuvanted FeLV vaccines, which though more efficacious, are perceived by some to lead to injection-site sarcomas. Accordingly, there remains a present need for an improved, safe nonadjuvanted FeLV vaccine, which while not inducing feline injection-site sarcomas still protects vaccinates from the debilitating disease state caused by FeLV infection as efficaciously as its inactivated whole-virus adjuvanted vaccine counterpart.

The citation of any reference herein should not be construed as an admission that such reference is available as "prior art" to the instant application.

SUMMARY OF THE INVENTION

Accordingly, the present invention provides vectors that encode one or more feline leukemia virus (FeLV) antigens. Such vectors can be used in immunogenic compositions comprising these vectors. The immunogenic compositions of the present invention may be used in vaccines. In one aspect of the present invention, a vaccine protects the vaccinated subject (e.g., mammal) against FeLV. In a particular embodiment of this type, the vaccinated subject is a feline. In a more particular embodiment, the vaccinated subject is a domestic cat. The present invention further provides combination vaccines for eliciting protective immunity against FeLV and other diseases, e.g., other feline infectious diseases. Methods of making and using the immunogenic compositions and vaccines of the present invention are also provided.

In specific embodiments, the vector is an alphavirus RNA replicon particle that encodes one or more antigens that originate from a feline pathogen. In particular embodiments, the feline pathogen is FeLV. In more particular embodiments, the alphavirus RNA replicon particles encode a FeLV glycoprotein (gp85). In related embodiments, the alphavirus RNA replicon particles encode an antigenic fragment of gp85. In a particular embodiment of this type, the antigenic fragment of gp85 is the FeLV glycoprotein gp70. In certain related embodiments, the antigenic fragment of gp85 is the FeLV glycoprotein gp45. In still more particular embodiments, the alphavirus RNA replicon particle is a Venezuelan Equine Encephalitis (VEE) alphavirus RNA replicon particle. In yet more specific embodiments the VEE alphavirus RNA replicon particle is a TC-83 VEE alphavirus RNA replicon particle. In other embodiments, the alphavirus RNA replicon particle is a Sindbis (SIN) alphavirus RNA replicon particle. In still other embodiments, the alphavirus RNA replicon particle is a Semliki Forest virus (SFV) alphavirus RNA replicon particle. In an alternative embodiment a naked DNA vector comprises a nucleic acid construct that encodes one or more antigens that originate from a feline pathogen. In particular embodiments of this type, the naked DNA vectors comprise a nucleic acid construct that encodes a FeLV gp85, or antigenic fragment thereof.

In certain embodiments an alphavirus RNA replicon particle of the present invention encodes one or more FeLV antigens or antigenic fragments thereof. In particular embodiments of this type, the alphavirus RNA replicon particles encode two to four FeLV antigens or antigenic fragments thereof. In other embodiments, immunogenic compositions comprise alphavirus RNA replicon particles that encode one or more FeLV antigens or antigenic fragments thereof. In related embodiments, the immunogenic compositions comprise alphavirus RNA replicon particles encodes two to four FeLV antigens or antigenic fragments thereof. In particular embodiments of this type, the alphavirus RNA replicon particles encode an FeLV glycoprotein (gp85) or an antigenic fragment thereof. In more particular embodiments of this type, the antigenic fragment of gp85 is the FeLV glycoprotein gp70. In certain related embodiments, the antigenic fragment of gp85 is the FeLV glycoprotein gp45. In more particular embodiments, the immunogenic composition comprises alphavirus RNA replicon particles that are Venezuelan Equine Encephalitis (VEE) alphavirus RNA replicon particles. In yet more specific embodiments the VEE alphavirus RNA replicon particles are TC-83 VEE alphavirus RNA replicon particles.

In still other embodiments, the immunogenic composition comprises two or more sets of alphavirus RNA replicon particles. In particular embodiments of this type, one set of alphavirus RNA replicon particles encodes a particular antigen, whereas the other set of alphavirus RNA replicon particles encodes a second antigen. In a specific embodiment of this type the first set of alphavirus RNA replicon particles encode the FeLV antigen or an antigenic fragment thereof, and the second set of alphavirus RNA replicon particles encode a feline calicivirus (FCV) antigen or an antigenic fragment thereof. In certain embodiments of this type, the FCV antigen originates from a virulent systemic feline calicivirus (VS-FCV) isolate. In other embodiments the FCV antigen originates from a classical (F9-like) feline calicivirus isolate. In yet other embodiments, the second set of alphavirus RNA replicon particles encode two FCV antigens, one of which originates from a virulent systemic feline calicivirus isolate, whereas the other originates from a classical (F9-like) feline calicivirus isolate.

In yet other embodiments, the immunogenic composition comprises one set of alphavirus RNA replicon particles that encode a first antigen, another set of alphavirus RNA replicon particles that encode a second antigen, and a third set of alphavirus RNA replicon particles that encode a third antigen. In a particular embodiment of this type, the first set of alphavirus RNA replicon particles encode the FeLV antigen or an antigenic fragment thereof, the second set of alphavirus RNA replicon particles encode a feline calicivirus (FCV) antigen which originates from a virulent systemic feline calicivirus or an antigenic fragment thereof, and the third set of alphavirus RNA replicon particles encode a feline calicivirus (FCV) antigen which originates from a classical (F9-like) feline calicivirus or an antigenic fragment thereof.

Accordingly, in particular embodiments in which the immunogenic compositions comprise multiple sets (e.g., 2-10) of alphavirus RNA replicon particles, in which the first set of alphavirus RNA replicon particles encode the FeLV antigen or an antigenic fragment thereof, the one or more other sets of alphavirus RNA replicon particles can encode one or more non-FeLV antigens. In certain embodiments of this type, the non-FeLV antigen is a protein antigen that originates from feline herpesvirus (FHV). In other embodiments, the non-FeLV antigen is a protein antigen that originates from feline calicivirus (FCV). In yet other embodiments, the non-FeLV antigen is a protein antigen that originates from feline pneumovirus (FPN). In still other embodiments, the non-FeLV antigen is a protein antigen that originates from feline parvovirus (FPV). In yet other embodiments, the non-FeLV antigen is a protein antigen that originates from feline infectious peritonitis virus (FIPV). In still other embodiments, the non-FeLV antigen is a protein antigen that originates from feline immunodeficiency virus. In still other embodiments, the non-FeLV antigen is a protein antigen that originates from borna disease virus (BDV). In yet other embodiments, the non-FeLV antigen is a protein antigen that originates from feline influenza virus. In still other embodiments, the non-FeLV antigen is a protein antigen that originates from feline panleukopenia virus (FPLV). In yet other embodiments the non-FeLV antigen is a protein antigen that originates from feline coronavirus (FCoV). In still other embodiments the non-FeLV antigen is a protein antigen that originates from feline rhinotracheitis virus (FVR). In yet other embodiments the non-FeLV antigen is a protein antigen that originates from *Chlamydophila felis*.

The present invention also includes all of the nucleic acid constructs of the present invention including synthetic messenger RNA, RNA replicons, as well as all of the alphavirus RNA replicon particles of the present invention, the naked DNA vectors, and the immunogenic compositions and/or vaccines that comprise the nucleic acid constructs (e.g., synthetic messenger RNA, RNA replicons), the alphavirus RNA replicon particles, and/or the naked DNA vectors of the present invention.

In particular embodiments, a nucleic acid construct of the present invention encodes one or more FeLV antigens or antigenic fragments thereof. In related embodiments of this type, the nucleic acid construct encodes two to four FeLV antigens or antigenic fragments thereof. In other embodiments, alphavirus RNA replicon particles comprise a nucleic acid construct that encodes one or more FeLV antigens or antigenic fragments thereof. In particular embodiments, alphavirus RNA replicon particles comprise a nucleic acid construct that encodes two to four FeLV antigens or antigenic fragments thereof.

In still other embodiments, the immunogenic compositions comprise alphavirus RNA replicon particles that comprise a nucleic acid construct that encodes two to four FeLV antigens or antigenic fragments thereof. In particular embodiments of this type, the alphavirus RNA replicon particles comprise a nucleic acid construct encoding an FeLV glycoprotein (gp85) or an antigenic fragment thereof. In a particular embodiment of this type, the antigenic fragment of gp85 is the FeLV glycoprotein gp70. In other related embodiments, the antigenic fragment of gp85 is the FeLV glycoprotein gp45. In more particular embodiments, the immunogenic composition comprises alphavirus RNA replicon particles that are Venezuelan Equine Encephalitis (VEE) alphavirus RNA replicon particles. In yet more specific embodiments the VEE alphavirus RNA replicon particles are TC-83 VEE alphavirus RNA replicon particles.

In yet other embodiments, the immunogenic composition comprises two or more sets of alphavirus RNA replicon particles. In particular embodiments of this type, one set of alphavirus RNA replicon particles comprises a first nucleic acid construct, whereas the other set of alphavirus RNA replicon particles comprise a second nucleic acid construct. In a specific embodiment of this type the first nucleic acid construct encodes the FeLV antigen or an antigenic fragment thereof, and the second nucleic acid construct encodes a feline calicivirus (FCV) antigen or an antigenic fragment thereof. In certain embodiments of this type, the FCV antigen originates from a virulent systemic feline calicivirus (VS-FCV) isolate. In other embodiments the FCV antigen originates from a classical (F9-like) feline calicivirus isolate. In yet other embodiments, the second nucleic acid construct encodes two FCV antigens, one of which originates from a virulent systemic feline calicivirus isolate, whereas the other originates from a classical (F9-like) feline calicivirus isolate.

In still other embodiments, the immunogenic composition comprises one set of alphavirus RNA replicon particles that comprise a first nucleic acid construct, another set of alphavirus RNA replicon particles that comprise a second nucleic acid construct, and a third set of alphavirus RNA replicon particles that comprise a third nucleic acid construct. In a particular embodiment of this type, the first nucleic acid construct encodes the FeLV antigen or an antigenic fragment thereof, the second nucleic acid construct encodes a feline calicivirus (FCV) antigen which originates from a virulent systemic feline calicivirus or an antigenic fragment thereof, and the third nucleic acid construct encodes a feline calicivirus (FCV) antigen which originates from a classical (F9-like) feline calicivirus or an antigenic fragment thereof.

In yet other embodiments, the immunogenic composition comprises one set of alphavirus RNA replicon particles that comprise a first nucleic acid construct, another set of alphavirus RNA replicon particles that comprise a second nucleic acid construct, a third set of alphavirus RNA replicon particles that comprise a third nucleic acid construct, and a fourth set of alphavirus RNA replicon particles that comprise a fourth nucleic acid construct. In yet other embodiments, the immunogenic composition comprises a set of alphavirus RNA replicon particles that comprise a first nucleic acid construct, another set of alphavirus RNA replicon particles that comprise a second nucleic acid construct, a third set of alphavirus RNA replicon particles that comprise a third nucleic acid construct, a fourth set of alphavirus RNA replicon particles that comprise a fourth nucleic acid construct, and a fifth set of alphavirus RNA replicon particles that comprise a fifth nucleic acid construct. In such embodiments, the nucleotide sequences of the first nucleic acid construct, the second nucleic acid construct, third nucleic acid construct, the fourth nucleic acid construct, and the fifth nucleic acid construct are all different.

Accordingly, an immunogenic composition of the present invention can contain alphavirus RNA replicon particles that comprise a nucleic acid construct that encodes at least one non-FeLV antigen for eliciting protective immunity to a non-FeLV pathogen. In particular embodiments of this type, the non-FeLV antigen is a protein antigen that originates from feline herpesvirus (FHV). In other embodiments, the non-FeLV antigen is a protein antigen that originates from feline calicivirus (FCV). In yet other embodiments, the non-FeLV antigen is a protein antigen that originates from feline pneumovirus (FPN). In still other embodiments, the non-FeLV antigen is a protein antigen that originates from feline parvovirus (FPV). In yet other embodiments, the non-FeLV antigen is a protein antigen that originates from feline infectious peritonitis virus (FIPV). In still other embodiments, the non-FeLV antigen is a protein antigen that originates from feline immunodeficiency virus. In still other embodiments, the non-FeLV antigen is a protein antigen that originates from borna disease virus (BDV). In yet other embodiments, the non-FeLV antigen is a protein antigen that originates from feline influenza virus. In still other embodiments, the non-FeLV antigen is a protein antigen that originates from feline panleukopenia virus (FPLV). In yet other embodiments the non-FeLV antigen is a protein antigen that originates from feline coronavirus (FCoV). In still other embodiments the non-FeLV antigen is a protein antigen that originates from feline rhinotracheitis virus (FVR). In still other embodiments the non-FeLV antigen is a protein antigen that originates from *Chlamydophila felis*.

The present invention further provides combination immunogenic compositions and/or vaccines (multivalent vaccines) that include alphavirus RNA replicon particles that encode an antigen or antigenic fragment thereof originating from FeLV together with one or more modified live (e.g., attenuated) or killed feline pathogens. In particular embodiments, the immunogenic compositions comprise a modified live or killed *Chlamydophila felis* combined with alphavirus RNA replicon particles that encode an antigen or antigenic fragment thereof originating from FeLV. In other embodiments, the immunogenic compositions comprise a modified live or killed feline rhinotracheitis Virus (FVR) combined with alphavirus RNA replicon particles that encode an antigen or antigenic fragment thereof originating from FeLV. In still other embodiments, the immunogenic compositions comprise a modified live or killed feline calicivirus (FCV) combined with alphavirus RNA replicon particles that encode an antigen or antigenic fragment thereof originating from FeLV. In yet other embodiments, the immunogenic compositions comprise a modified live or killed feline panleukopenia virus (FPL) combined with alphavirus RNA replicon particles that encode an antigen or antigenic fragment thereof originating from FeLV. In still other embodiments, the immunogenic compositions comprise a modified live or killed *Chlamydophila felis*, a modified live or killed FVR, a modified live or killed FCV, a modified live or killed FPL, and alphavirus RNA replicon particles that encode an antigen or antigenic fragment thereof originating from FeLV. In particular embodiments of this type, the feline antigen of the FeLV is the FeLV viral glycoprotein (gp85). In certain embodiments, vaccines comprise an immunologically effective amount of one or more of these immunogenic compositions.

In particular embodiments the FeLV antigen is the FeLV glycoprotein (gp85). In specific embodiments of this type, the FeLV glycoprotein gp85 comprises an amino acid sequence comprising 95% identity or more with the amino acid sequence of SEQ ID NO: 2. In more specific embodiments of this type, the FeLV glycoprotein (gp85) comprises the amino acid sequence of SEQ ID NO: 2. In even more specific embodiments of this type the FeLV glycoprotein (gp85) is encoded by the nucleotide sequence of SEQ ID NO: 1 or SEQ ID NO: 10. In related embodiments, the FeLV glycoprotein gp70 comprises an amino acid sequence comprising 95% identity or more with the amino acid sequence of SEQ ID NO: 4. In more specific embodiments of this type, the FeLV glycoprotein (gp85) comprises the amino acid sequence of SEQ ID NO: 4. In even more specific embodiments of this type the FeLV glycoprotein (gp70) is encoded by the nucleotide sequence of SEQ ID NO: 3 or SEQ ID NO: 11.

The present invention further comprises vaccines and multivalent vaccines comprising the immunogenic compositions of the present invention. In particular embodiments, the vaccines are nonadjuvanted vaccine. In certain embodiments, the vaccine aids in the prevention of disease due to FeLV. In related embodiments, antibodies are induced in a feline subject when the feline is immunized with the vaccine.

The present invention also provides methods of immunizing a feline against a feline pathogen, e.g., FeLV, comprising administering to the feline an immunologically effective amount of a vaccine or multivalent of the present invention. In particular embodiments the vaccine is administered via intramuscular injection. In alternative embodiments the vaccine is administered via subcutaneous injection. In other embodiments the vaccine is administered via intravenous injection. In still other embodiments the vaccine is administered via intradermal injection. In yet other embodiments the vaccine is administered via oral administration. In still other embodiments the vaccine is administered via intranasal administration. In specific embodiments, the feline is a domestic cat.

The vaccines and multivalent vaccines of the present invention can be administered as a primer vaccine and/or as a booster vaccine. In specific embodiments, a vaccine of the present invention is administered as a one shot vaccine (one dose), without requiring subsequent administrations. In certain embodiments, in the case of the administration of both a primer vaccine and a booster vaccine, the primer vaccine and the booster vaccine can be administered by the identical route. In certain embodiments of this type, the primer vaccine and the booster vaccine are both administered by subcutaneous injection. In alternative embodiments, in the case of the administration of both a primer vaccine and a booster vaccine, the administration of the primer vaccine can be performed by one route and the booster vaccine by another route. In certain embodiments of this type, the primer vaccine can be administered by subcutaneous injection and the booster vaccine can be administered orally.

The invention further provides for a method of immunizing a feline against FeLV comprising injecting the feline with an immunologically effective amount of the above described inventive vaccines. In particular embodiments the vaccines can include from about $1 \times 10^4$ to about $1 \times 10^{10}$ RPs or higher, for example. In more particular embodiments the vaccines can include from about $1 \times 10^5$ to about $1 \times 10^9$ RPs. In even more particular embodiments the vaccines can include from about $1 \times 10^6$ to about $1 \times 10^8$ RPs. In particular embodiments the feline is a domestic cat.

In particular embodiments the vaccines of the present invention are administered in 0.05 mL to 3 mL doses. In more particular embodiments the dose administered is 0.1 mL to 2 mLs. In still more particular embodiments the dose administered is 0.2 mL to 1.5 mLs. In even more particular embodiments the dose administered is 0.3 to 1.0 mLs. In still more particular embodiments the dose administered is 0.4 mL to 0.8 mLs. In yet more particular embodiments the dose administered is 0.5 mL to 1.5 mLs.

These and other aspects of the present invention will be better appreciated by reference to the following Detailed Description.

DETAILED DESCRIPTION OF THE INVENTION

The present invention provides an improved, safe nonadjuvanted FeLV vaccine. In one aspect, the vaccines of the present invention do not induce feline injection-site sarcomas, yet still provide protection to the vaccinates from the debilitating disease state caused by FeLV infection as efficaciously as an inactivated whole-virus adjuvanted vaccine.

Accordingly, the vaccine compositions of the present invention include an immunologically effective amount of a vector encoding an antigen from one or more strains of feline leukemia virus that aids in eliciting protective immunity in the recipient vaccinated animal. Furthermore, the present invention provides new immunologic compositions to improve the reliability of vaccination to aid in the reduction of antigenemia in a feline infected by FeLV and to thereby yield a transient antigenemia and/or lead to the elimination of the infection. In a particular aspect of the present invention, the vaccines comprise an alphavirus RNA replicon particle (RP) encoding the FeLV viral glycoprotein (gp85). In more specific embodiments, the vaccines comprise alphavirus RNA replicon particles (RPs) that comprise the capsid protein and glycoproteins of Venezuelan Equine Encephalitis Virus (VEE) and encode the FeLV viral glycoprotein (gp85) and/or an antigenic fragment thereof (e.g., gp70 or gp45). In even more specific embodiments, the vaccines comprise alphavirus RNA replicon particles (RPs) that comprise the capsid protein and glycoproteins of the avirulent TC-83 strain of VEE and encode the FeLV viral glycoprotein (gp85) and/or an antigenic fragment thereof (e.g., gp70 or gp45). In another aspect of the present invention, the vaccines comprise naked DNA vectors that encode the FeLV viral glycoprotein (gp85) and/or an antigenic fragment thereof (e.g., gp70 or gp45). The vaccines of the present invention can be administered to a feline in the absence of an adjuvant and still effectively aid in the protection of the vaccinated feline against FeLV.

In order to more fully appreciate the invention, the following definitions are provided.

The use of singular terms for convenience in description is in no way intended to be so limiting. Thus, for example, reference to a composition comprising "a polypeptide" includes reference to one or more of such polypeptides. In addition, reference to an "alphavirus RNA replicon particle" includes reference to a plurality of such alphavirus RNA replicon particles, unless otherwise indicated.

As used herein the term "approximately" is used interchangeably with the term "about" and signifies that a value is within fifty percent of the indicated value i.e., a composition containing "approximately" $1\times10^8$ alphavirus RNA replicon particles per milliliter contains from $0.5\times10^8$ to $1.5\times10^8$ alphavirus RNA replicon particles per milliliter.

As used herein, the term "feline" refers to any member of the Felidae family. Domestic cats, pure-bred and/or mongrel companion cats, and wild or feral cats are all felines.

As used herein, the term "replicon" refers to a modified RNA viral genome that lacks one or more elements (e.g., coding sequences for structural proteins) that if they were present, would enable the successful propagation of the parental virus in cell cultures or animal hosts. In suitable cellular contexts, the replicon will amplify itself and may produce one or more sub-genomic RNA species.

As used herein, the term "alphavirus RNA replicon particle", abbreviated "RP", is an alphavirus-derived RNA replicon packaged in structural proteins, e.g., the capsid and glycoproteins, which also are derived from an alphavirus, e.g., as described by Pushko et al., [*Virology* 239(2):389-401 (1997)]. An RP cannot propagate in cell cultures or animal hosts (without a helper plasmid or analogous component), because the replicon does not encode the alphavirus structural components (e.g., capsid and glycoproteins).

The term "non-FeLV", is used to modify terms such as pathogen, and/or antigen (or immunogen) to signify that the respective pathogen, and/or antigen (or immunogen) is neither an FeLV pathogen nor a FeLV antigen (or immunogen) and that a non-FeLV protein antigen (or immunogen) does not originate from an FeLV.

The terms "originate from", "originates from" and "originating from" are used interchangeably with respect to a given protein antigen and the pathogen or strain of that pathogen that naturally encodes it, and as used herein signify that the unmodified and/or truncated amino acid sequence of that given protein antigen is encoded by that pathogen or strain of that pathogen. The coding sequence within a nucleic acid construct of the present invention for a protein antigen originating from a pathogen may have been genetically manipulated so as to result in a modification and/or truncation of the amino acid sequence of the expressed protein antigen relative to the corresponding sequence of that protein antigen in the pathogen or strain of pathogen (including naturally attenuated strains) it originates from.

As used herein, the terms "protecting", or "providing protection to", or "eliciting protective immunity to", "aids in prevention of disease", and "aids in the protection" do not require complete protection from any indication of infection. For example, "aids in the protection" can mean that the protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

As used herein, a "vaccine" is a composition that is suitable for application to an animal, e.g., feline (including, in certain embodiments, humans, while in other embodiments being specifically not for humans) comprising one or more antigens typically combined with a pharmaceutically acceptable carrier such as a liquid containing water, which upon administration to the animal induces an immune response strong enough to minimally aid in the protection from a disease arising from an infection with a wild-type micro-organism, i.e., strong enough for aiding in the prevention of the disease, and/or preventing, ameliorating or curing the disease.

As used herein, a multivalent vaccine is a vaccine that comprises two or more different antigens. In a particular embodiment of this type, the multivalent vaccine stimulates the immune system of the recipient against two or more different pathogens.

The terms "adjuvant" and "immune stimulant" are used interchangeably herein, and are defined as one or more substances that cause stimulation of the immune system. In this context, an adjuvant is used to enhance an immune response to one or more vaccine antigens/isolates. Accordingly, "adjuvants" are agents that nonspecifically increase an immune response to a particular antigen, thus reducing the quantity of antigen necessary in any given vaccine, and/or the frequency of injection necessary in order to generate an adequate immune response to the antigen of interest. In this context, an adjuvant is used to enhance an immune response to one or more vaccine antigens/isolates. The American Association of Feline Practitioners Feline Vaccination Guidelines suggest the use of nonadjuvanted FeLV vaccines [*AAFP Feline Advisory Panel,* 15: 785-808 (2013)].

As used herein, a "nonadjuvanted vaccine" is a vaccine or a multivalent vaccine that does not contain an adjuvant.

As used herein, the term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient animal, e.g., feline.

Parenteral administration" includes subcutaneous injections, submucosal injections, intravenous injections, intramuscular injections, intradermal injections, and infusion.

As used herein the term "antigenic fragment" in regard to a particular protein (e.g., a protein antigen) is a fragment of that protein that is antigenic, i.e., capable of specifically interacting with an antigen recognition molecule of the immune system, such as an immunoglobulin (antibody) or T cell antigen receptor. For example, an antigenic fragment of an FeLV viral glycoprotein (gp85) is a fragment of the gp85 protein that is antigenic. Preferably, an antigenic fragment of the present invention is immunodominant for antibody and/or T cell receptor recognition. In particular embodiments, an antigenic fragment with respect to a given protein antigen is a fragment of that protein that retains at least 25% of the antigenicity of the full length protein. In preferred embodiments an antigenic fragment retains at least 50% of the antigenicity of the full length protein. In more preferred embodiments, an antigenic fragment retains at least 75% of the antigenicity of the full length protein. Antigenic fragments can be as small as 20 amino acids or at the other extreme, be large fragments that are missing as little as a single amino acid from the full-length protein. In particular embodiments the antigenic fragment comprises 25 to 150 amino acid residues. In other embodiments, the antigenic fragment comprises 50 to 250 amino acid residues. The gp45 glycoprotein and the gp70 glycoprotein are antigenic fragments of the gp85 glycoprotein.

As used herein one amino acid sequence is 100% "identical" or has 100% "identity" to a second amino acid sequence when the amino acid residues of both sequences are identical. Accordingly, an amino acid sequence is 50% "identical" to a second amino acid sequence when 50% of the amino acid residues of the two amino acid sequences are identical. The sequence comparison is performed over a contiguous block of amino acid residues comprised by a given protein, e.g., a protein, or a portion of the polypeptide being compared. In a particular embodiment, selected deletions or insertions that could otherwise alter the correspondence between the two amino acid sequences are taken into account.

As used herein, nucleotide and amino acid sequence percent identity can be determined using C, MacVector (MacVector, Inc. Cary, N.C. 27519), Vector NTI (Informax, Inc. MD), Oxford Molecular Group PLC (1996) and the Clustal W algorithm with the alignment default parameters, and default parameters for identity. These commercially available programs can also be used to determine sequence similarity using the same or analogous default parameters. Alternatively, an Advanced Blast search under the default filter conditions can be used, e.g., using the GCG (Genetics Computer Group, Program Manual for the GCG Package, Version 7, Madison, Wis.) pileup program using the default parameters.

As used herein, the term "inactivated" microorganism is used interchangeably with the term "killed" microorganism. For the purposes of this invention, an "inactivated" microorganism is an organism which is capable of eliciting an immune response in an animal, but is not capable of infecting the animal. An antigen of the present invention (e.g., an inactivated feline panleukopenia virus) may be inactivated by an agent selected from the group consisting of binary ethyleneimine, formalin, beta-propiolactone, thimerosal, or heat. In a particular embodiment, inactivated feline calicivirus isolates combined with an RP of the present invention are inactivated by binary ethyleneimine.

The alphavirus RNA replicon particles of the present invention may be lyophilized and rehydrated with a sterile water diluent. On the other hand, when the alphavirus RNA replicon particles are stored separately, but intend to be mixed with other vaccine components prior to administration, the alphavirus RNA replicon particles can be stored in the stabilizing solution of those components, e.g., a high sucrose solution.

A vaccine of the present invention can be readily administered by any standard route including intravenous, intramuscular, subcutaneous, oral, intranasal, intradermal, and/or intraperitoneal vaccination. The skilled artisan will appreciate that the vaccine composition is preferably formulated appropriately for each type of recipient animal and route of administration.

Thus, the present invention also provides methods of immunizing a feline against FeLV and/or other feline pathogens. One such method comprises injecting a feline with an immunologically effective amount of a vaccine of the present invention, so that the feline produces appropriate FeLV antibodies.

Multivalent Vaccines:

The present invention also provides multivalent vaccines. For example, the coding sequence of a protein antigen or antigenic fragment thereof, or combination of such coding sequences of protein antigens useful in a feline vaccine can be added to an alphavirus RNA replicon particle (RP) or combined in the same RP as one that encodes a feline antigen of the FeLV [e.g., the FeLV viral glycoprotein (gp85)] in the vaccine. Accordingly, such multivalent vaccines are included in the present invention.

Examples of pathogens that one or more of such protein antigens can originate from include feline rhinotracheitis Virus (FVR), feline calicivirus (FCV), feline panleukopenia Virus (FPL) feline herpesvirus (FHV), other FeLV strains, feline parvovirus (FPV), feline infectious peritonitis virus (FIPV), feline immunodeficiency virus, borna disease virus (BDV), rabies virus, feline influenza virus, canine influenza virus, avian influenza, canine pneumovirus, feline pneumovirus, *Chlamydophila felis* (FKA *Chlamydia psittaci*), *Bordetella bronchiseptica*, and *Bartonella* spp. (e.g., *B. henselae*). In particular embodiments, a coding sequence for a capsid protein or analogous protein from one or more of these feline or canine pathogens can be inserted into the same RP as the FeLV antigen. Alternatively, or in combination therewith, a coding sequence for a capsid protein or analogous protein from one or more of these feline or canine pathogens can be inserted into one or more other RPs, which can be combined with the RP that encodes the FeLV antigen in a vaccine.

In addition, an alphavirus RNA replicon particle(RP) that encodes a feline antigen of the FeLV [e.g., the FeLV viral glycoprotein (gp85)] can be added together with one or more other live, attenuated virus isolates such as a live attenuated other FCV strain, a live attenuated feline herpesvirus and/or a live attenuated feline parvovirus and/or a live, attenuated feline leukemia virus, and/or a live, attenuated feline infectious peritonitis virus and/or a live, attenuated feline immunodeficiency virus and/or a live, attenuated borna disease virus and/or a live, attenuated rabies virus, and/or a live, attenuated feline influenza virus and/or a live, attenuated canine influenza virus, and/or a live, attenuated avian influenza, and/or a live, attenuated canine pneumovirus, and/or a live, attenuated feline pneumovirus. In addition, a live, attenuated *Chlamydophila felis*, and/or a live, attenuated *Bordetella bronchiseptica* and/or a live, attenuated *Bartonella* spp. (e.g., *B. henselae*) can also be included in such multivalent vaccines.

Furthermore, an alphavirus RNA replicon particle (RP) that encodes a feline antigen of the FeLV [e.g., the FeLV viral glycoprotein (gp85)] can be added together with one or more other killed virus isolates such as a killed FCV strain, and/or a killed feline herpesvirus and/or a killed feline parvovirus and/or a killed feline leukemia virus, and/or a killed feline infectious peritonitis virus and/or a killed feline immunodeficiency virus and/or a killed borna disease virus and/or a killed rabies virus, and/or a killed feline influenza virus and/or a killed canine influenza virus, and/or a killed avian influenza virus, and/or a killed canine pneumovirus, and/or a killed feline pneumovirus. In addition, bacterins of *Chlamydophila felis*, and/or *Bordetella bronchiseptica* and/or *Bartonella* spp. (e.g., *B. henselae*) can also be included in such multivalent vaccines.

It is also to be understood that this invention is not limited to the particular configurations, process steps, and materials disclosed herein as such configurations, process steps, and materials may vary somewhat.

It is also to be understood that the terminology employed herein is used for the purpose of describing particular embodiments only and is not intended to be limiting, since the scope of the present invention will be limited only by the appended claims and equivalents thereof.

SEQUENCE TABLE

| SEQ ID NO: | Description | Type |
|---|---|---|
| 1 | FeLV viral glycoprotein (gp85) | nucleic acid DNA |
| 2 | FeLV viral glycoprotein (gp85) | amino acid |
| 3 | FeLV viral glycoprotein (gp70) | nucleic acid DNA |
| 4 | FeLV viral glycoprotein (gp70) | amino acid |
| 5 | Feline Calicivirus (VS-FCV) | nucleic acid DNA |
| 6 | Feline Calicivirus (VS-FCV) | amino acid |
| 7 | Feline Calicivirus (F9-like) | nucleic acid DNA |
| 8 | Feline Calicivirus (F9-like) | amino acid |
| 9 | GGCGCGCCGCACC | nucleic acid |
| 10 | FeLV viral glycoprotein (gp85) | nucleic acid RNA |
| 11 | FeLV viral glycoprotein (gp70) | nucleic acid RNA |
| 12 | Feline Calicivirus (VS-FCV) | nucleic acid RNA |
| 13 | Feline Calicivirus (F9-like) | nucleic acid RNA |
|  | TTAATTAA | nucleic acid |

SEQUENCES

Feline Leukemia Virus envelope glycoprotein (gp85) SEQ ID NO: 1

```
atggagtcaccaacacaccctaaaccttctaaagacaaaaccctctcgtggaatctcgccttccttgt
gggcatcctgttcacaatcgacatcggcatggccaacccttcgccgcatcagatctacaatgtgacat
gggtcattactaatgtgcagacaaacacccaggcaaatgctacttctatgcttggtactctgactgat
gcttatccaaccctgcacgtcgacctttgcgatctcgtcggtgacacatgggagcccatcgtgctgaa
tccaactaatgtcaaacatggtgccaggtattcttctagcaaatacgggtgtaagaccactgatcgga
agaaacagcaacaaacctacccattctacgtgtgcccgggtcacgcaccgtccctgggtccgaaggga
acacattgtgggggagcccaagacggtttttgcgctgcttggggttgtgaaacaacggagaagcctg
gtggaagcctacctcatcttgggactacattactgtgaaaagaggctctagccaggataacagctgcg
aaggaaagtgtaatcccctggtgcttcaattcacccagaaaggccggcaggcatcatgggatggaccg
aaaatgtggggacttagactctatcgcaccggatacgacccccatcgctctgtttactgtgtcacgcca
agtctccaccattactccgcacaggccatggggccgaatctggtcctccccgatcagaagccaccct
cacggcaaagtcaaaccggctcaaaagtggccacccaacggccccagacaaatgagtccgcacctagg
tcagtggcacctacaacaatgggtccaaagcggatcggaaccggagacaggctcattaacctcgtgca
agggacttatctggcccttaacgctactgaccccaacaagaccaaggattgctggctctgccttgtga
gcagacctcctactatgagggatcgccattctcggaaactactcaaatcagaccaaccccctccg
tcgtgtctgagcacccccagcacaagcttactattttcagaagtcagtggacagggaatgtgcatcgg
aaccgtgccaaagactcatcaagccctttgcaacaaaactcaacaagggcacactggagctcattatc
tcgccgcacctaacgggacctactgggcttgcaatactggattgaccccgtgtatctctatggccgtg
ctgaattggacttccgacttctgcgtgcttattgagctttggcctagagtgacataccatcagcctga
gtacgtctatacccatttcgccaaggcagtcagattccggcgggagcctatctccctgactgtggcct
tgatgctcggtggactgacagtgggaggaattgcagctggagctggaactggaaccaaggccctgctc
gaaactgctcagttccggcagctgcagatggccatgcacactgacatccaggctctggaggaatcaat
ttcagcccttgagaaaagcttgacctcgctgtctgaagtggtcctccaaaacaggcgcggtttggaca
tcctgttccttcaagagggtggtctgtgcgccgctctcaaggaggaatgctgtttctacgctgaccat
accgggctggtgcgcgataacatggcaaagctgcgggaacgcttgaaacagaggcagcaactgttcga
ctctcagcagggatggttcgagggctggtttaacaagagcccatggtttaccactctgatctcttcaa
tcatgggtccactgctcatcctgcttctgattcttctcttcggaccgtgtattctcaacaggctggtg
cagtttgtcaaggacagaatctcggtggtccaggccctgattcttactcagcagtatcagcagattaa
gcagtacgaccccgatcggccttga
```

Feline Leukemia Virus envelope glycoprotein (gp85) SEQ ID NO: 2

```
MESPTHPKPSKDKTLSWNLAFLVGILFTIDIGMANPSPHQIYNVTWVITNVQTNTQANAT
SMLGTLTDAYPTLHVDLCDLVGDTWEPIVLNPTNVKHGARYSSSKYGCKTTDRKKQQQTY
PFYVCPGHAPSLGPKGTHCGGAQDGFCAAWGCETTGEAWWKPTSSWDYITVKRGSSQDNS
CEGKCNPLVLQFTQKGRQASWDGPKMWGLRLYRTGYDPIALFTVSRQVSTITPPQAMGPN
LVLPDQKPPSRQSQTGSKVATQRPQTNESAPRSVAPTTMGPKRIGTGDRLINLVQGTYLA
LNATDPNKTKDCWLCLVSRPPYYEGIAILGNYSNQTNPPPSCLSTPQHKLTISEVSGQGM
CIGTVPKTHQALCNKTQQGHTGAHYLAAPNGTYWACNTGLTPCISMAVLNWTSDFCVLIE
LWPRVTYHQPEYVYTHFAKAVRFRREPISLTVALMLGGLTVGGIAAGVGTGTKALLETAQ
FRQLQMAMHTDIQALEESISALEKSLTSLSEVVLQNRRGLDILFLQEGGLCAALKEECCF
YADHTGLVRDNMAKLRERLKQRQQLFDSQQGWFEGWFNKSPWFTTLISSIMGPLLILLLI
LLFGPCILNRLVQFVKDRISVVQALILTQQYQQIKQYDPDRP*
```

-continued

| SEQUENCES |
| --- |

Feline Leukemia Virus envelope glycoprotein (gp85) SEQ ID NO: 10
auggagucaccaacacacccuaaaccuucuaaagacaaaacccucucguggaaucucgccuuccuugu
gggcauccuguucacaaucgacaucggcauggccaacccuucgccgcaucagaucuacaaugugacau
gggucauuacuaaugugcagacaaacacccaggcaaaugcuacuucuaugcuugguacucugacugau
gcuuauccaacccugcacgucgaccuuugcgaucucgucggugacacaugggagcccaucgugcugaa
uccaacuaaugucaaacauggugccagguauucuucuagcaaauacggguguaagaccacugaucgga
agaaacagcaacaaaccuacccauucuacgugugcccgggucacgcaccgucccugggucgaagga
acacauuguggggggagcccaagacgguuuuugcgcugcuugggguugugaaacaaccggagaagccug
guggaagccuaccucaucuugggacuacauuacugugaaaagaggcucuagccaggauaacagcugcg
aaggaaaguguaauccccuggugcuucaauucacccagaaaggccggcaggcaucaugggauggaccg
aaaaugugggggacuuagacucuaucgcaccggauacgaccccaucgcucuguuuacugugucacgcca
agucuccaccauuacuccgccacaggccaugggggccgaaucugguccuccccgaucagaagccacccu
cacggcaaagucaaaccggcucaaaaguggccacccaacggccccagacaaaugaguccgcaccuagg
ucaguggcaccuacaacaaugggguccaaagcggaucggaaccggagacaggcucauuaaccucgugca
agggacuuaucuggcccuuaacgcuacugaccccaacaagaccaaggauugcuggcucugccuuguga
gcagaccuccuuacuaugaggggaucgccauucucggaaacuacucaaaucagaccaacccccuccg
ucgugucugagcacccccccagcacaagcuuacuauuucagaagucaguggacagggaaugugcaucgg
aaccgugccaaagacucaucaagcccuuugcaacaaaacucaacaagggcacacuggagcucauuauc
ucgccgcaccuaacgggaccuacugggcuugcaauacuggauugaccccguguaucucuauggccgug
cugaauuggacuuccgacuucugcgugcuuauugagcuuuggccuagagugacauaccaucagccuga
guacgucuauacccauuucgccaaggcagucagauuccggcgggagccuaucucccugacuguggccu
ugaugcucgguggacugacagugggaggaauugcagcuggagucggaacuggaaccaaggcccugcuc
gaaacugcucaguuccggcagcugcagauggccaugcacacugacauccaggcucuggaggaaucaau
uucagcccuugagaaaagcuugaccucgcugucugaagugguccuccaaaacaggcgcgguuuggaca
uccuguuccuucaagagggugguucugugcgccgcucucaaggaggaaugcuguuucuacgcugaccau
accgggcuggugcgcgauaacauggcaaagcugcgggaacgcuugaaacagaggcagcaacuguucga
cucucagcagggaugguucgagggcugguuuaacaagagcccaugguuuaccacucugaucucuucaa
ucaugggucccacugcucauccugcuucugauucuucucuucggaccguguauucucaacaggcuggug
caguuugucaaggacagaaucucgguggucccaggcccugauucuuacucagcaguaucagcagauuaa
gcaguacgaccccgaucggccuuga Feline Leukemia Virus envelope glycoprotein (gp70) SEQ ID NO: 3
aatcctagtccacaccaaatatataatgtaacttgggtaataaccaatgtacaaactaacacc
caagctaacgccacctctatgttaggaaccttaaccgatgcctaccctaccctacatgttgac
ttatgtgacctagtgggagacacctgggaacctatagtcctaaacccaaccaatgtaaaacac
ggggcacgttactcctcctcaaaatatggatgtaaaactacagatagaaaaaaacagcaacag
acataccccttttacgtctgccccggacatgccccctcgttggggccaaagggaacacattgt
ggaggggcacaagatgggttttgtgccgcatggggatgtgagaccaccggagaagcttggtgg
aagcccacctcctcatgggactatatcacagtaaaaagagggagtagtcaggacaatagctgt
gagggaaaatgcaacccccctggttttgcagttcacccagaagggaagacaagcctcttgggac
ggacctaagatgtggggattgcgactataccgtacaggatatgaccctatcgctttattcacg
gtgtcccggcaggtatcaaccattacgccgcctcaggcaatgggaccaaacctagtcttacct
gatcaaaaaccccccatcccgacaatctcaaacagggtccaaagtggcgacccagaggccccaa
acgaatgaaagcgccccaaggtctgttgcccccaccaccatgggtcccaaacggattgggacc
ggagataggttaataaatttagtacaagggacatacctagccttaaatgccaccgaccccaac
aaaactaaagactgttggctctgcctggtttctcgaccaccctattacgaagggattgcaatc
ttaggtaactacagcaaccaaacaaacccccccccatcctgcctatctactccgcaacacaaa
ctaactatatctgaagtatcagggcaaggaatgtgcatagggactgttcctaaaacccaccag
gctttgtgcaataagacacaacagggacatacaggggcgcactatctagccgcccccaacggc
acctattgggcctgtaacactggactcaccccatgcatttccatggcggtgctcaattggacc
tctgatttttgtgtcttaatcgaattatggcccagagtgacttaccatcaacccgaatatgtg
tacacacattttgccaaagctgtcaggttccgaaga Feline Leukemia Virus envelope glycoprotein (gp70) SEQ ID NO: 4
NPSPHQIYNVTWVITNVQTNTQANATSMLGTLTDAYPTLHVDLCDLVGDTWEPIVLNPTNVKHGARYSSS
KYGCKTTDRKKQQQTYPFYVCPGHAPSLGPKGTHCGGAQDGFCAAWGCETTGEAWWKPTSSWDYITVKRG
SSQDNSCEGKCNPLVLQFTQKGRQASWDGPKMWGLRLYRTGYDPIALFTVSRQVSTITPPQAMGPNLVLP
DQKPPSRQSQTGSKVATQRPQTNESAPRSVAPTTMGPKRIGTGDRLINLVQGTYLALNATDPNKTKDCWL
CLVSRPPYYEGIAILGNYSNQTNPPPSCLSTPQHKLTISEVSGQGMCIGTVPKTHQALCNKTQQGHTGAH
YLAAPNGTYWACNTGLTPCISMAVLNWTSDFCVLIELWPRVTYHQPEYVYTHFAKAVRFRR Feline Leukemia Virus envelope glycoprotein (gp70) SEQ ID NO: 11
aauccuaguccacaccaaauauauaauguaacuuggguaauaaccaauguacaaacuaacacc
caagcuaacgccaccucuauguuaggaaccuuaaccgaugccuacccuacccuacauguugac
uuaugugaccuagugggagacaccugggaaccuauaguccuaaacccaaccaauguaaaacac
ggggcacguuacuccuccucaaaauauggauguaaaacuacagauagaaaaaaacagcaacag
acauaccccuuuuacgucugccccggacaugcccccucguuggggccaaagggaacacauugu
ggaggggcacaagauggguuuugugccgcauggggaugugagaccaccggagaagcuuggugg
aagcccaccuccucaugggacuauaucacaguaaaaagagggaguagucaggacaauagcugu
gagggaaaaugcaacccccugguuuugcaguucacccagaagggaagacaagccucuugggac
ggaccuaagaugugggggauugcgacuauaccguacaggauaugacccuaucgcuuuauucacg
gugucccggcagguaucaaccauuacgccgccucaggcaaugggaccaaaccuagucuuaccu
gaucaaaaaccccccaucccgacaaucucaaacaggguccaaaguggcgacccagaggccccaa
acgaaugaaagcgccccaaggucuguugcccccaccaccauggguccccaaacggauugggacc
ggagauagguuaauaaauuuaguacaagggacauaccuagccuuaaaugccaccgaccccaac
aaaacuaaagacuguuggcucugccugguuucucgaccacccuauuacgaagggauugcaauc -continued

| SEQUENCES |
| --- | uuagguaacuacagcaaccaaacaaaccccccccccauccugccuaucuacuccgcaacacaaa
cuaacuauaucugaaguaucagggcaaggaaugugcauagggacuguuccuaaaacccaccag
gcuuugugcaauaagacacaacagggacauacaggggcgcacuaucuagccgcccccaacggc
accuauugggccuguaacacuggacucaccccaugcauuuccauggcggugcucaauuggacc
ucugauuuuugugucuuaaucgaauuauggcccagagugacuuaccaucaacccgaauaugug
uacacacauuuugccaaagcugucagguuccgaaga Feline Calicivirus (VS-FCV) capsid (SEQ ID NO: 5)
atggctgacgacggatctgtgaccaccccagaacaaggaacaatggtcggaggagtgatt
gccgaacccagcgctcagatgtcaactgcggcggacatggcctccggaaagtcggtggac
tccgagtgggaagccttcttctcgttccacacgtccgtgaactggagcacctccgaaacc
caaggaaagatcctcttcaagcagtccctgggtcccctgctgaacccgtacctggagcac
atcagcaagctgtacgtcgcttggagcgggtcgatcgaagtgcgattttccatctcggga
agcggcgtgttcggtggtaaactggccgccatcgtcgtgccgcctggtgtcgaccctgtc
cagtcaacctccatgctgcagtacccgcacgtcctgttcgacgcaagacaagtggagcca
gtgatcttctccatcccggacctccgcaacagcctgtatcacttgatgtccgataccgat
accacttccctcgtgatcatggtgtacaacgatctgatcaacccgtacgccaatgactcc
aacagctcgggttgcatcgtgaccgtcgaaacgaagcctggcatcgatttcaagtttcat
ctgctgaaaccgcccggatccatgcttactcacgggtccatcccttccgatctgatcccc
aagagctcctccctgtggattgggaaccgccactggaccgatattaccgatttcgtgatt
cggcctttcgtgttccaagccaaccggcacttcgacttcaaccaggagactgccggctgg
tcaactccacggttccgcccattggccgtgactgtgtcgcagtcaaagggagccaagctc
gggaacggcatcgccaccgactacattgtgcctggaatccccgacggatggcctgatact
accatccccaccaagctgacccctaccggagattacgccatcacctcctccgacggcaat
gatattgaaaccaagctggaatacgagaacgcggacgtgattaagaacaacaccaacttc
cgctccatgtatatctgcggaagcctccagagggcttggggcgacaagaagatcagcaac
accgggttcatcactaccggagtgatttctgacaactccatcagcccttcgaacacaatt
gaccagtccaagatcgtggtgtaccaggacaaccatgtcaattcggaggtccagactagc
gacatcactcttgccatcctgggctacaccggaattggagaagaggccataggcgccaac
cgggactccgtcgtgagaatttccgtgcttccggaaactggagcaaggggcggaaatcac
cccatcttctacaaaaattccatgaagctgggctacgtgatctcctccattgacgtgttc
aactcccaaatcctccacacctcgcgccagctgtcactgaacaactacttgttgcccccct
gactccttcgcggtgtaccggattattgacagcaacggatcatggttcgacattgggatt
gacagcgatgggttttcattcgtgggcgtgtcgtcatttccaaagctggagtttccgctg
tccgcctcatacatgggcatccagctcgcaaagatccggctggcgtccaacatccggtca
tccatgactaagctgtga Feline Calicivirus (VS-FCV) capsid (SEQ ID NO: 6)
MADDGSVTTPEQGTMVGGVIAEPSAQMSTAADMASGKSVDSEWEAFFSFHTSVNWSTSET
QGKILFKQSLGPLLNPYLEHISKLYVAWSGSIEVRFSISGSGVFGGKLAAIVVPPGVDPV
QSTSMLQYPHVLFDARQVEPVIFSIPDLRNSLYHLMSDTDTTSLVIMVYNDLINPYANDS
NSSGCIVTVETKPGIDFKFHLLKPPGSMLTHGSIPSDLIPKSSSLWIGNRHWTDITDFVI
RPFVFQANRHFDFNQETAGWSTPRFRPLAVTVSQSKGAKLGNGIATDYIVPGIPDGWPDT
TIPTKLTPTGDYAITSSDGNDIETKLEYENADVIKNNTNFRSMYICGSLQRAWGDKKISN
TGFITTGVISDNSISPSNTIDQSKIVVYQDNHVNSEVQTSDITLAILGYTGIGEEAIGAN
RDSVVRISVLPETGARGGNHPIFYKNSMKLGYVISSIDVFNSQILHTSRQLSLNNYLLPP
DSFAVYRIIDSNGSWFDIGIDSDGFSFVGVSSFPKLEFPLSASYMGIQLAKIRLASNIRS
SMTKL Feline Calicivirus (VS-FCV) capsid (SEQ ID NO: 12)
auggcugacgacggaucugugaccaccccagaacaaggaacaauggucggaggagugauu
gccgaacccagcgcucagaugucaacugcggcggacauggccuccggaaagucgguggac
uccgagugggaagccuucuucucguuccacacguccgugaacuggagcaccuccgaaacc
caaggaaagauccucuucaagcagucccugggucccugcugaacccguaccuggagcac
aucagcaagcuguacgucgcuuggagcgggucgaucgaagugcgauuuuccaucucggga
agcggcguguucggugguaaacuggccgccaucgucgugccgccuggugucgacccuguc
cagucaaccuccaugcugcaguacccgcacguccuguucgacgcaagacaaguggagcca
gugaucuucuccaucccggaccuccgcaacagccuguaucacuugauguccgauaccgau
accacuucccucgugaucaugguguacaacgaucugaucaacccguacgccaaugacucc
aacagcucggguugcaucgugaccgucgaaacgaagccuggcaucgauuucaaguuucau
cugcugaaaccgcccggauccaugcuuacucacggguccaucccuuccgaucugaucccc
aagagcuccucccuguggauugggaaccgccacuggaccgauauuaccgauuucgugauu
cggccuuucguguuccaagccaaccggcacuucgacuucaaccaggagacugccggcugg
ucaacuccacgguuccgcccauuggccgugacugugucgcagucaaagggagccaagcuc
gggaacggcaucgccaccgacuacauugugccuggaauccccgacggauggccugauacu
accauccccaccaagcugaccccuaccggagauuacgccaucaccuccuccgacggcaau
gauauugaaaccaagcuggaauacgagaacgcggacgugauuaagaacaacaccaacuuc
cgcuccauguauaucugcggaagccuccagagggcuuggggcgacaagaagaucagcaac
accggguucaucacuaccggagugauuucugacaacuccaucagcccuucgaacacaauu
gaccaguccaagaucgugguguaccaggacaaccaugucaauucggagguccagacuagc
gacaucacucuugccauccugggcuacaccggaauuggagaagaggccauaggcgccaac
cgggacuccgucgugagaauuuccgugcuuccggaaacuggagcaaggggcggaaaucac
cccaucuucuacaaaaauuccaugaagcugggcuacgugaucuccuccauugacguguuc
aacucccaaauccuccacaccucgcgccagcugucacugaacaacuacuuguugccccccu
gacuccuucgcgguguaccggauuauugacagcaacggaucaugguucgacauugggauu
gacagcgauggguuuucauucgugggcgugucgucauuuccaaagcuggaguuuccgcug
uccgccucauacaugggcauccagcucgcaaagauccggcuggcguccaacauccgguca -continued

| SEQUENCES |
|---| uccaugacuaagcuguga

Feline Calicivirus (F9-like) capsid (SEQ ID NO: 7)
atgactgccccggaacaaggaacgatggtcggaggagtgattgcagaaccgtcagcacag
atgtccaccgctgccgacatggccactggaaagagcgtggactccgaatgggaagccttc
ttctccttccacacttcggtcaactggtcgactagcgaaacccaggggaagattttgttc
aagcaatccctcggccctctgctgaacccctacctggagcatctggccaagctgtacgtg
gcatggtcgggcagcatcgaagtgcgctttagcatttccggctccggagtgttcggggga
aagcttgctgccattgtcgtgccgccaggagtggacccggtgcagtccacttctatgctc
caatacccgcatgtcctgttcgacgccagacaggtggagcctgtgatcttttgcctgccg
gatctcaggtccaccctgtatcacctcatgtccgacaccgacaccacctcgctcgtgatc
atggtgtacaacgacctgatcaacccctacgctaacgacgccaacagctcaggttgcatt
gtgactgtcgaaaccaagccaggccctgacttcaagtttcatttgctgaagccgcccggt
tccatgctgacccacggctcgatcccatccgacctgatccccaagacgagctccctgtgg
atcggaaaccgctactggtccgatattaccgacttcgtgatcagaccattcgtgttccaa
gccaaccgccatttcgacttcaaccaggaaaccgcaggatggtcgacccctcgattccgc
ccgatttcagtgaccatcaccgaacagaacggcgcgaagctgggaattggcgtggcgacc
gactacatcgtgccgggaatcccggatggatggcctgatacgaccattcccggggagctg
atccctgccggggactacgccatcaccaacggtactggaaacgacatcaccactgccacc
ggttacgacaccgccgacatcataaagaacaacaccaacttcagaggaatgtacatttgc
ggctccctgcaacgcgcttggggtgacaaaaagatctcgaacactgccttcatcacaaca
gcgactctggacggcgataacaacaacaagatcaatccttgtaataccatcgaccagtcc
aaaatcgtggtgttccaggataaccacgtgggaaagaaggcgcagacctccgacgacact
ctggcgctgcttggctacaccgggatcggcgagcaggccattggaagcgatcggatcgg
gtcgtgcggatctccaccctccccgagactggagcaaggggaggcaaccaccccatcttt
tacaaaaacagcattaagctcggatacgtcatccgctccatcgatgtgttcaactctcaa
atcctgcacacttcgcggcagctgtccctgaaccactacctcttgccgcccgactccttc
gccgtctaccggatcattgattcgaacgggagctggttcgacatcggcattgatagcgat
ggcttctcgtttgtgggcgtgtcgggcttcgggaagctggagttcccactgagcgcctca
tacatgggtatccagctggccaagatcaggctggcctccaacatccgctcacctatgact
aagctgtga Feline Calicivirus (F9-like) capsid (SEQ ID NO: 8)
MTAPEQGTMVGGVIAEPSAQMSTAADMATGKSVDSEWEAFFSFHTSVNWSTSETQGKILF
KQSLGPLLNPYLEHLAKLYVAWSGSIEVRFSISGSGVFGGKLAAIVVPPGVDPVQSTSML
QYPHVLFDARQVEPVIFCLPDLRSTLYHLMSDTDTTSLVIMVYNDLINPYANDANSSGCI
VTVETKPGPDFKFHLLKPPGSMLTHGSIPSDLIPKTSSLWIGNRYWSDITDFVIRPFVFQ
ANRHFDFNQETAGWSTPRFRPISVTITEQNGAKLGIGVATDYIVPGIPDGWPDTTIPGEL
IPAGDYAITNGTGNDITTATGYDTADIIKNNTNFRGMYICGSLQRAWGDKKISNTAFITT
ATLDGDNNNKINPCNTIDQSKIVVFQDNHVGKKAQTSDDTLALLGYTGIGEQAIGSDRDR
VVRISTLPETGARGGNHPIFYKNSIKLGYVIRSIDVFNSQILHTSRQLSLNHYLLPPDSF
AVYRIIDSNGSWFDIGIDSDGFSFVGVSGFGKLEFPLSASYMGIQLAKIRLASNIRSPMT
KL Feline Calicivirus (F9-like) capsid (SEQ ID NO: 13)
augacugccccggaacaaggaacgauggucggaggagugauugcagaaccgucagcacag
auguccaccgcugccgacauggccacuggaaagagcguggacuccgaaugggaagccuuc
uucuccuuccacacuucggucaacuggucgacuagcgaaacccaggggaagauuuuguuc
aagcaaucccucggcccucugcugaaccccuaccuggagcaucuggccaagcuguacgug
gcauggucgggcagcaucgaagugcgcuuuagcauuuccggcuccggaguguucggggga
aagcuugcugccauugucgugccgccaggaguggacccggugcaguccacuucuaugcuc
caauacccgcauguccuguucgacgccagacagguggagccugugaucuuuugccugccg
gaucucagguccacccuguaucaccucauguccgacaccgacaccaccucgcucgugauc
augguguacaacgaccugaucaaccccuacgcuaacgacgccaacagcucagguugcauu
gugacugucgaaaccaagccaggcccugacuucaaguuucauuugcugaagccgcccggu
uccaugcugacccacggcucgaucccauccgaccugauccccaagacgagcucccugugg
aucggaaaccgcuacugguccgauauuaccgacuucgugaucagaccauucguguuccaa
gccaaccgccauuucgacuucaaccaggaaaccgcaggauggucgaccccucgauuccgc
ccgauuucagugaccaucaccgaacagaacggcgcgaagcugggaauuggcguggcgacc
gacuacaucgugccgggaaucccggauggauggccugauacgaccauucccggggagcug
aucccugccggggacuacgccaucaccaacgguacuggaaacgacaucaccacugccacc
gguuacgacaccgccgacaucauaaagaacaacaccaacuucagaggaauguacauuugc
ggcucccugcaacgcgcuuggggugacaaaaagaucucgaacacugccuucaucacaaca
gcgacucuggacggcgauaacaacaacaagaucaauccuuguaauaccaucgaccagucc
aaaaucgugguguuccaggauaaccacgugggaaagaaggcgcagaccuccgacgacacu
cuggcgcugcuuggcuacaccgggaucggcgagcaggccauuggaagcgaucggaucgg
gucgugcggaucuccacccuccccgagacuggagcaaggggaggcaaccaccccaucuuu
uacaaaaacagcauuaagcucggauacgucauccgcuccaucgauguguucaacucucaa
auccugcacacuucgcggcagcugucccugaaccacuaccucuugccgcccgacuccuuc
gccgucuaccggaucauugauucgaacgggagcugguucgacaucggcauugauagcgau
ggcuucucguuugugggcgugucgggcuucgggaagcuggaguucccacugagcgccuca
uacauggguauccagcuggccaagaucaggcuggccuccaacauccgcucaccuaugacu
aagcuguga The following examples serve to provide further appreciation of the invention but are not meant in any way to restrict the effective scope of the invention.

EXAMPLES

Example 1

Incorporation of the Coding Sequences for FeLV GP85 into the Alphavirus RNA Replicon Particles Introduction RNA viruses have been used as vector-vehicles for introducing vaccine antigens, which have been genetically engineered into their genomes. However, their use to date has been limited primarily to incorporating viral antigens into the RNA virus and then introducing the virus into a recipient host. The result is the induction of protective antibodies against the incorporated viral antigens. Alphavirus RNA replicon particles have been used to encode pathogenic antigens. Such alphavirus replicon platforms have been developed from several different alphaviruses, including Venezuelan equine encephalitis virus (VEE) [Pushko et al., *Virology* 239:389-401 (1997)], Sindbis (SIN) [Bredenbeek et al., *Journal of Virology* 67:6439-6446 (1993) the contents of which are hereby incorporated herein in their entireties], and Semliki Forest virus (SFV) [Liljestrom and Garoff, *Biotechnology* (NY) 9:1356-1361 (1991), the contents of which are hereby incorporated herein in their entireties]. Moreover, alphavirus RNA replicon particles are the basis for several USDA-licensed vaccines for swine and poultry. These include: Porcine Epidemic Diarrhea Vaccine, RNA Particle (Product Code 19U5.P1), Swine Influenza Vaccine, RNA (Product Code 19A5.D0), Avian Influenza Vaccine, RNA (Product Code 1905.D0), and Prescription Product, RNA Particle (Product Code 9PP0.00).

Alphavirus RNA Replicon Particle Construction

An amino acid sequence for FeLV gp85 were used to generate codon-optimized (feline codon usage) nucleotide sequences in silico. Optimized sequences were prepared as synthetic DNA by a commercial vendor (ATUM, Newark, Calif.). Accordingly, a synthetic gene was designed based on the amino acid sequence of gp85. The construct (gp85_wt) was wild-type amino acid sequence [SEQ ID NO: 2], codon-optimized for feline, with flanking sequence appropriate for cloning into the alphavirus replicon plasmid.

The VEE replicon vectors designed to express FeLV gp85 were constructed as previously described [see, U.S. Pat. No. 9,441,247 B2; the contents of which are hereby incorporated herein by reference in their entireties], with the following modifications. The TC-83-derived replicon vector "pVEK" [disclosed and described in U.S. Pat. No. 9,441,247 B2] was digested with restriction enzymes AscI and PacI. A DNA plasmid containing the codon-optimized open reading frame nucleotide sequence of the FeLV gp85 genes, with 5' flanking sequence (5'-GGCGCGCCGCACC-3') [SEQ ID NO: 9] and 3' flanking sequence (5'-TTAATTAA-3'), was similarly digested with restriction enzymes AscI and PacI. The synthetic gene cassette was then ligated into the digested pVEK vector, and the resulting clone was re-named "pVHV-FeLV gp85". The "pVHV" vector nomenclature was chosen to refer to pVEK-derived replicon vectors containing transgene cassettes cloned via the AscI and PacI sites in the multiple cloning site of pVEK.

Production of TC-83 RNA replicon particles (RP) was conducted according to methods previously described [U.S. Pat. No. 9,441,247 B2 and U.S. Pat. No. 8,460,913 B2; the contents of which are hereby incorporated herein by reference]. Briefly, pVHV replicon vector DNA and helper DNA plasmids were linearized with NotI restriction enzyme prior to in vitro transcription using MegaScript T7 RNA polymerase and cap analog (Promega, Madison, Wis.). Importantly, the helper RNAs used in the production lack the VEE subgenomic promoter sequence, as previously described [Kamrud et al., *J Gen Virol.* 91(Pt 7):1723-1727 (2010)]. Purified RNA for the replicon and helper components were combined and mixed with a suspension of Vero cells, electroporated in 4 mm cuvettes, and returned to OptiPro® SFM cell culture media (Thermo Fisher, Waltham Mass.). Following overnight incubation, alphavirus RNA replicon particles were purified from the cells and media by passing the suspension through a ZetaPlus BioCap depth filter (3M, Maplewood, Minn.), washing with phosphate buffered saline containing 5% sucrose (w/v), and finally eluting the retained RP with 400 mM NaCl buffer. Eluted RP were formulated to a final 5% sucrose (w/v), passed through a 0.22 micron membrane filter, and dispensed into aliquots for storage. Titer of functional RP was determined by immunofluorescence assay on infected Vero cell monolayers.

Example 2

Comparative Efficacy and Safety of FeLV Vaccines in Cats

A vaccine comprising an alphavirus RNA replicon particle (RP) comprising the capsid protein and glycoproteins of the avirulent TC-83 strain of Venezuelan Equine Encephalitis Virus (VEE) and encoding the FeLV viral glycoprotein (gp85), was formulated in 5% sucrose. The liquid vaccine was frozen for storage before use. This vaccine was compared with a commercially available vaccine comprising a recombinant canary pox encoding FeLV, as shown in Table 1 below. Five groups of eight feline subjects were vaccinated either with a single dose at 8-9 weeks, or in a prime/boost regimen of 8-9 weeks of age and then 21 days later. The doses for each experimental vaccinate group is provided in Table 1 below.

TABLE 1

| VACCINATION PROTOCOL | | | | |
|---|---|---|---|---|
| Vaccinate Group | No. of Animals | Vaccine | RP/dose | Vaccination Days |
| 1 | 8 | RP-FeLV | $4.35 \times 10^8$ | 0, 21 |
| 2 | 8 | RP-FeLV | $3.55 \times 10^7$ | 0, 21 |
| 3 | 8 | RP-FeLV | $1.5 \times 10^8$ | 21 (one shot) |
| 4 | 8 | PureVax ® # | Does not apply | 0, 21 |
| 5 | 8 | Placebo | none | 0, 21 |

A vaccine containing a recombinant canary pox encoding FeLV sold by Merial ®

All cats were subcutaneously vaccinated with 1.0 mL of their respective vaccine regimen. Cats were 8-9 weeks of age at the time of the initial vaccination (including cats in Group 3). The cats of Group 4 were vaccinated at the times provided with the quantity of vaccine as directed on the label of the commercial vaccine. Following the vaccination the cats were observed for adverse reactions to the vaccines by observing the general health daily, as well as palpating the site of injection for the two days following each vaccination and twice per week for two weeks following each vaccination. No adverse reactions were observed for any of the vaccines.

All cats were challenged with a virulent culture of FeLV four weeks after the booster vaccination (four weeks after the one-shot vaccination for the Group 3 cats). The cats were challenged on four separate days over one week (study days 49, 52, 54 and 56) by administering 1.0 mL of challenge virus by the oronasal route (0.3 mL in each nostril and 0.4 mL orally). Three weeks after challenge serum samples were collected each week through ten weeks post-challenge. Serum samples were tested by ELISA for the presence of FeLV p27 antigen. An animal is considered infected with FeLV if it is persistently antigenemic. Antigenemia is defined as a positive p27 ELISA result for three consecutive weeks or on five or more occasions during the eight week testing period. An FeLV vaccine must protect 75% of the cats vaccinated with the test product for USDA licensure. In addition, in order for the challenge to be regarded as valid, 80% of the control cats must be persistently antigenemic [see, Shipley et al., *JAVMA*, Vol. 199, No. 10, (Nov. 15, 1991)]. The results of the challenge are summarized in the Table 2 below.

TABLE 2

VACCINATION AND CHALLENGE

| Treatment Group | Vaccine | RP dose | % Cats Antigenemic | % Cats Protected |
|---|---|---|---|---|
| 1 | RP-FeLV | $4.35 \times 10^8$ | 0% | 100% |
| 2 | RP-FeLV | $3.55 \times 10^7$ | 0% | 100% |
| 3 | RP-FeLV | $1.5 \times 10^8$ (one shot)* | 13% | 87% |
| 4 | PureVax ® # | Does not apply | 43% | 57% |
| 5 | Placebo | Does not apply | 88% | 12% |

A vaccine containing a recombinant canary pox encoding FeLV sold by Merial ®
*All other groups received a two-dose regimen, see, Table 1 above.

As Table 2 demonstrates, the RP-FeLV vaccines protected 100% of the cats when administered in a two-dose regimen (i.e., primary and booster vaccination) at both doses tested. Moreover, the RP-FeLV vaccine protected 87% of the cats when administered as a single dose. In direct contrast, the commercially available vaccine only protected 57% of the cats, even with a two-dose regimen. In addition, the challenge is regarded as valid because greater than 80% of the control cats were persistently antigenemic [see, Table 2]. Finally, all of the RP-FeLV vaccine formulations were found safe in cats.

Example 3

Determination of the Dose Dependence of an RP-FeLV Vaccine by Vaccination and Challenge The RP-FeLV vaccine of Example 2 was formulated in a vaccine formulation that included enzymatically hydrolyzed casein (NZ-amine), gelatin, and sucrose. The vaccine was then lyophilized. Four groups of ten cats each were vaccinated as summarized in Table 3 below:

TABLE 3

VACCINATION PROTOCOL

| Treatment Group | No. of Animals | Vaccine | RP/dose | Vaccination Days |
|---|---|---|---|---|
| 1 | 10 | RP-FeLV | $1.1 \times 10^5$ | 0, 21 |
| 2 | 10 | RP-FeLV | $2.1 \times 10^6$ | 0, 21 |
| 3 | 10 | RP-FeLV | $6.5 \times 10^7$ | 0, 21 |
| 4 | 10 | Non-vaccinated Controls | None | NA |

All cats were vaccinated with 1.0 mL of respective test product, subcutaneously. The cats were 8-9 weeks of age at the time of initial vaccination. Following the vaccination the cats were observed for adverse reactions to the vaccines by observing their general daily health, as well as palpating the site of injection for the two days following each vaccination and twice per week for the two weeks following each vaccination. No adverse reactions to any of the vaccines were observed.

All of the cats were challenged with a virulent culture of FeLV three weeks after the booster vaccination. Cats were challenged on four separate days over one week (study days 42, 45, 47 and 49) by administering 1.0 mL of challenge virus by the oronasal route (0.3 mL in each nostril and 0.4 mL orally). Three weeks after challenge serum samples were collected each week through twelve weeks post-challenge. Serum samples were tested by ELISA for the presence of FeLV p27 antigen. An animal is considered infected with FeLV if it is found to be persistently antigenemic. Antigenemia is defined as a positive p27 ELISA result for three consecutive weeks, or on five or more occasions during the eight-week testing period. For USDA licensure an FeLV vaccine must protect 75% of the cats vaccinated with the test product. For the challenge to be considered valid, 80% of the control cats must be persistently antigenemic [Shipley et al., *JAVMA*, Vol. 199, No. 10, Nov. 15, 1991]. The results of the challenge are summarized in the Table 4 below:

TABLE 4

DOSE DEPENDENCE OF RP-FELV

| Treatment Group | Vaccine | RP/dose | % Cats Antigenemic | % Cats Protected |
|---|---|---|---|---|
| 1 | RP-FeLV | $1.1 \times 10^5$ | 10% | 90% |
| 2 | RP-FeLV | $2.1 \times 10^6$ | 0% | 100% |
| 3 | RP-FeLV | $6.5 \times 10^7$ | 0% | 100% |
| 4 | Non-vaccinated Controls | None | 90% | 10% |

In this study of short term immunity, the minimum protective dose of the RP-FeLV vaccine for 100% protection of the cats was between about $1.0 \times 10^5$ to about $2.0 \times 10^6$ RPs, when administered in a two dose (primary and booster vaccination) regimen. The challenge was valid because at least 80% of the control cats were persistently antigenemic. All RP-FeLV vaccine formulations tested were safe in cats.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

It is further to be understood that all base sizes or amino acid sizes, and all molecular weight or molecular mass values, given for nucleic acids or polypeptides are approximate, and are provided for description.

I claim:

1. An immunogenic composition comprising a Venezuelan Equine Encephalitis (VEE) alphavirus RNA replicon particle that encodes a feline leukemia virus (FeLV) glycoprotein (gp85) that comprises an amino acid sequence comprising at least 95% identity with the amino acid sequence of SEQ ID NO: 2.

2. An immunogenic composition comprising a Venezuelan Equine Encephalitis (VEE) alphavirus RNA replicon particle that encodes an antigenic fragment of a feline leukemia virus (FeLV) glycoprotein (gp85) that comprises an amino acid sequence comprising at least 95% identity with the amino acid sequence of SEQ ID NO: 4.

3. A vaccine to aid in the prevention of disease due to FeLV comprising the immunogenic composition of claim 1, and a pharmaceutically acceptable carrier.

4. The vaccine of claim 3, wherein an antibody is induced in a feline when said feline is immunized with the vaccine.

5. The vaccine composition of claim 3 that further comprises at least one non-FeLV antigen for eliciting protective immunity to a non-FeLV feline pathogen.

6. The vaccine of claim 5, wherein the non-FeLV feline pathogen is selected from the group consisting of feline herpesvirus (FHV), feline calicivirus (FCV), feline pneumovirus (FPN), feline parvovirus (FPV), feline infectious peritonitis virus (FIPV), feline immunodeficiency virus, borna disease virus (BDV), feline influenza virus, feline panleukopenia virus (FPLV), feline coronavirus (FCoV), feline rhinotracheitis virus (FVR), *Chlamydophila felis*, and any combination thereof.

7. The vaccine of claim 6, wherein the non-FeLV antigen is a killed or attenuated non-FeLV antigen selected from the group of killed or attenuated non-FeLV antigens consisting of feline herpesvirus (FHV), feline calicivirus (FCV), feline pneumovirus (FPN), feline parvovirus (FPV), feline infectious peritonitis virus (FIPV), feline immunodeficiency virus, borna disease virus (BDV), feline influenza virus, feline panleukopenia virus (FPLV), feline coronavirus (FCoV), feline rhinotracheitis virus (FVR), *Chlamydophila felis*, and any combination thereof.

8. The vaccine of claim 7, wherein the attenuated non-FeLV antigen is a modified live feline pathogen selected from the group consisting of a modified live *Chlamydophila felis*, a modified live feline rhinotracheitis Virus (FVR), a modified live feline calicivirus (FCV), a modified live feline panleukopenia virus (FPL), a modified live feline herpesvirus (FHV), a modified live feline pneumovirus (FPN), a modified live feline parvovirus (FPV), a modified live feline infectious peritonitis virus (FIPV), a modified live feline immunodeficiency virus, a modified live borna disease virus (BDV), a modified live feline coronavirus (FCoV), and a modified live feline influenza virus.

9. The vaccine composition of claim 3, that further comprises an alphavirus RNA replicon particle comprising a nucleotide sequence encoding at least one protein antigen or an antigenic fragment thereof that originates from a non-FeLV antigen.

10. The vaccine of claim 9, wherein the protein antigen or an antigenic fragment thereof that originates from a non-FeLV feline pathogen selected from the group consisting of feline herpesvirus (FHV), feline calicivirus (FCV), feline pneumovirus (FPN), feline parvovirus (FPV), feline infectious peritonitis virus (FIPV), feline immunodeficiency virus, borna disease virus (BDV), feline influenza virus, feline panleukopenia virus (FPLV), feline coronavirus (FCoV), feline rhinotracheitis virus (FVR), *Chlamydophila* fells, and any combination thereof.

11. The vaccine composition of claim 3, that is a nonadjuvanted vaccine.

12. A method of immunizing a feline against a pathogenic FeLV comprising administering to the feline an immunologically effective amount of the vaccine of claim 11.

13. The vaccine of claim 3, further comprising a modified live feline calicivirus (FCV), a modified live feline panleukopenia virus (FPLV), a modified live feline rhinotracheitis virus (FVR), and an attenuated live strain of *Chlamydophila felis*.

14. The vaccine composition of claim 13, that is a nonadjuvanted vaccine.

15. A method of immunizing a feline against a pathogenic FeLV comprising administering to the feline an immunologically effective amount of the vaccine of claim 13.

16. A vaccine to aid in the prevention of disease due to FeLV comprising the immunogenic composition of claim 2, and a pharmaceutically acceptable carrier.

17. A method of immunizing a feline against a pathogenic FeLV comprising administering to the feline an immunologically effective amount of the vaccine of claim 16.

18. The vaccine of claim 3, further comprising a modified live feline pathogen selected from the group consisting of a modified live feline viral rhinotracheitis virus (FVR), a modified live feline panleukopenia virus (FPLV), a modified live feline calicivirus (FCV), and a modified live *Chlamydophila felis*, and any combination thereof, and a pharmaceutically acceptable carrier.

19. A method of immunizing a feline against a pathogenic FeLV comprising administering to the feline an immunologically effective amount of the vaccine of claim 18.

20. A method of immunizing a feline against a pathogenic FeLV comprising administering to the feline an immunologically effective amount of the vaccine of claim 3.

* * * * *